(12) United States Patent
Nau, Jr. et al.

(10) Patent No.: US 9,358,069 B2
(45) Date of Patent: Jun. 7, 2016

(54) SURGICAL FORCEPS

(71) Applicant: COVIDIEN LP, Mansfield, MA (US)

(72) Inventors: William H. Nau, Jr., Longmont, CO (US); Arlen J. Reschke, Longmont, CO (US); Robert M. Sharp, Boulder, CO (US); Duane E. Kerr, Loveland, CO (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 14/519,414

(22) Filed: Oct. 21, 2014

(65) Prior Publication Data

US 2015/0038954 A1 Feb. 5, 2015

Related U.S. Application Data

(63) Continuation of application No. 13/324,863, filed on Dec. 13, 2011, now Pat. No. 8,864,753.

(51) Int. Cl.
*A61B 19/00* (2006.01)
*A61B 18/22* (2006.01)
(Continued)

(52) U.S. Cl.
CPC ............... *A61B 18/22* (2013.01); *A61B 17/285* (2013.01); *A61B 18/1445* (2013.01); *A61B 18/1447* (2013.01); *A61B 18/1815* (2013.01); *A61B 18/20* (2013.01); *A61B 2017/2933* (2013.01); *A61B 2018/00011* (2013.01);
(Continued)

(58) Field of Classification Search
CPC ........... A61B 18/1445; A61B 18/1447; A61B 2018/145; A61B 17/28; A61B 17/29; A61B 17/00234; A61B 17/00353; A61B 2017/2901; A61B 2017/2926; A61B 2017/2932; A61B 2017/2933
USPC ............. 606/1, 13–17, 20–23, 130, 205–211; 607/88, 89, 96, 100, 101
See application file for complete search history.

(56) References Cited

U.S. PATENT DOCUMENTS

| 1,731,069 A | 10/1929 | Herman |
| D249,549 S | 9/1978 | Pike |

(Continued)

FOREIGN PATENT DOCUMENTS

| CN | 201299462 | 9/2009 |
| DE | 2415263 A1 | 10/1975 |

(Continued)

OTHER PUBLICATIONS

U.S. Appl. No. 13/050,182, Glenn A. Horner.
(Continued)

*Primary Examiner* — Ahmed Farah

(57) ABSTRACT

A forceps includes an end effector assembly having first and second jaw members movable relative to one another between a spaced-apart position, a first approximated position, and a second approximated position. One or both of the jaw members including a first stop member coupled thereto and disposed between the jaw members. The first stop member is longitudinally translatable along a surface of the at least one jaw member from a first position, wherein the first stop member inhibits approximation of the jaw members beyond the first approximated position, and a second position, wherein the first stop member inhibits approximation of the jaw members beyond the second approximated position.

19 Claims, 9 Drawing Sheets

(51) Int. Cl.
*A61B 18/14* (2006.01)
*A61B 17/285* (2006.01)
*A61B 18/20* (2006.01)
*A61B 17/29* (2006.01)
*A61B 18/18* (2006.01)
*A61B 18/00* (2006.01)

(52) U.S. Cl.
CPC *A61B 2018/0063* (2013.01); *A61B 2018/0097* (2013.01); *A61B 2018/00601* (2013.01); *A61B 2018/00994* (2013.01); *A61B 2018/1455* (2013.01); *A61B 2018/1807* (2013.01); *A61B 2019/302* (2013.01); *A61B 2019/304* (2013.01); *A61B 2019/306* (2013.01)

(56) References Cited

U.S. PATENT DOCUMENTS

| | | | |
|---|---|---|---|
| D263,020 S | 2/1982 | Rau, III | |
| D295,893 S | 5/1988 | Sharkany et al. | |
| D295,894 S | 5/1988 | Sharkany et al. | |
| D298,353 S | 11/1988 | Manno | |
| D299,413 S | 1/1989 | DeCarolis | |
| D343,453 S | 1/1994 | Noda | |
| 5,318,589 A * | 6/1994 | Lichtman | A61B 17/29 600/564 |
| D348,930 S | 7/1994 | Olson | |
| D349,341 S | 8/1994 | Lichtman et al. | |
| D354,564 S | 1/1995 | Medema | |
| D358,887 S | 5/1995 | Feinberg | |
| 5,626,578 A * | 5/1997 | Tihon | A61B 18/1442 606/48 |
| 5,626,607 A | 5/1997 | Malecki et al. | |
| D384,413 S | 9/1997 | Zlock et al. | |
| 5,762,609 A | 6/1998 | Benaron et al. | |
| H1745 H | 8/1998 | Paraschac | |
| D402,028 S | 12/1998 | Grimm et al. | |
| 5,876,401 A * | 3/1999 | Schulze | A61B 17/07207 606/41 |
| D408,018 S | 4/1999 | McNaughton | |
| D416,089 S | 11/1999 | Barton et al. | |
| 5,984,939 A * | 11/1999 | Yoon | A61B 17/12013 606/139 |
| D424,694 S | 5/2000 | Tetzlaff et al. | |
| D425,201 S | 5/2000 | Tetzlaff et al. | |
| H1904 H | 10/2000 | Yates et al. | |
| D449,886 S | 10/2001 | Tetzlaff et al. | |
| D453,923 S | 2/2002 | Olson | |
| D454,951 S | 3/2002 | Bon | |
| D457,958 S | 5/2002 | Dycus et al. | |
| D457,959 S | 5/2002 | Tetzlaff et al. | |
| H2037 H | 7/2002 | Yates et al. | |
| 6,454,762 B1 | 9/2002 | Rosler et al. | |
| D465,281 S | 11/2002 | Lang | |
| D466,209 S | 11/2002 | Bon | |
| D493,888 S | 8/2004 | Reschke | |
| D496,997 S | 10/2004 | Dycus et al. | |
| D499,181 S | 11/2004 | Dycus et al. | |
| D502,994 S | 3/2005 | Blake, III | |
| D509,297 S | 9/2005 | Wells | |
| D525,361 S | 7/2006 | Hushka | |
| D531,311 S | 10/2006 | Guerra et al. | |
| D533,274 S | 12/2006 | Visconti et al. | |
| D533,942 S | 12/2006 | Kerr et al. | |
| D535,027 S | 1/2007 | James et al. | |
| D538,932 S | 3/2007 | Malik | |
| 7,195,631 B2 * | 3/2007 | Dumbauld | A61B 17/29 604/22 |
| D541,418 S | 4/2007 | Schechter et al. | |
| D541,611 S | 5/2007 | Aglassinger | |
| D541,938 S | 5/2007 | Kerr et al. | |
| D545,432 S | 6/2007 | Watanabe | |
| D547,154 S | 7/2007 | Lee | |
| D564,662 S | 3/2008 | Moses et al. | |
| D567,943 S | 4/2008 | Moses et al. | |
| D575,395 S | 8/2008 | Hushka | |
| D575,401 S | 8/2008 | Hixson et al. | |
| D582,038 S | 12/2008 | Swoyer et al. | |
| 7,491,202 B2 | 2/2009 | Odom et al. | |
| D617,900 S | 6/2010 | Kingsley et al. | |
| D617,901 S | 6/2010 | Unger et al. | |
| D617,902 S | 6/2010 | Twomey et al. | |
| D617,903 S | 6/2010 | Unger et al. | |
| D618,798 S | 6/2010 | Olson et al. | |
| 7,731,717 B2 | 6/2010 | Odom et al. | |
| D621,503 S | 8/2010 | Otten et al. | |
| 7,776,037 B2 | 8/2010 | Odom | |
| D627,462 S | 11/2010 | Kingsley | |
| D628,289 S | 11/2010 | Romero | |
| D628,290 S | 11/2010 | Romero | |
| D630,324 S | 1/2011 | Reschke | |
| 7,931,649 B2 | 4/2011 | Couture et al. | |
| D649,249 S | 11/2011 | Guerra | |
| D649,643 S | 11/2011 | Allen, IV et al. | |
| D661,394 S | 6/2012 | Romero et al. | |
| 8,864,753 B2 | 10/2014 | Nau, Jr. et al. | |
| 2003/0114851 A1 | 6/2003 | Truckai et al. | |
| 2005/0033359 A1 * | 2/2005 | Dycus | A61B 17/0057 606/213 |
| 2006/0224158 A1 | 10/2006 | Odom et al. | |
| 2008/0319442 A1 | 12/2008 | Unger et al. | |
| 2011/0112569 A1 * | 5/2011 | Friedman | A61B 5/042 606/205 |

FOREIGN PATENT DOCUMENTS

| | | |
|---|---|---|
| DE | 02514501 A1 | 10/1976 |
| DE | 2627679 A1 | 1/1977 |
| DE | 03423356 C2 | 6/1986 |
| DE | 03612646 A1 | 4/1987 |
| DE | 8712328 U1 | 2/1988 |
| DE | 04303882 C2 | 2/1995 |
| DE | 04403252 A1 | 8/1995 |
| DE | 4434938 C1 | 2/1996 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19751108 A1 | 5/1999 |
| DE | 19946527 C1 | 7/2001 |
| DE | 20121161 U1 | 4/2002 |
| DE | 10045375 C2 | 10/2002 |
| DE | 202007009165 U1 | 8/2007 |
| DE | 202007009317 U1 | 8/2007 |
| DE | 202007009318 U1 | 8/2007 |
| DE | 10031773 B4 | 11/2007 |
| DE | 202007016233 U1 | 1/2008 |
| DE | 19738457 B4 | 1/2009 |
| DE | 102004026179 B4 | 1/2009 |
| DE | 102208018406 | 7/2009 |
| EP | 1 159 926 A2 | 12/2001 |
| EP | 1707143 | 10/2006 |
| EP | 2353534 A1 | 8/2011 |
| JP | 61-501068 | 9/1984 |
| JP | 10-24051 A | 1/1989 |
| JP | 11-47150 A | 6/1989 |
| JP | 6-502328 | 3/1992 |
| JP | 5-5106 | 1/1993 |
| JP | 05-40112 | 2/1993 |
| JP | 0006030945 A | 2/1994 |
| JP | 6-121797 A | 5/1994 |
| JP | 6-285078 A | 10/1994 |
| JP | 6-511401 | 12/1994 |
| JP | 06343644 A | 12/1994 |
| JP | 07265328 A | 10/1995 |
| JP | 8-56955 | 5/1996 |
| JP | 08252263 A | 10/1996 |
| JP | 8-289895 A | 11/1996 |
| JP | 8-317934 A | 12/1996 |
| JP | 8-317936 A | 12/1996 |
| JP | 9-10223 C | 1/1997 |
| JP | 9-122138 A | 5/1997 |
| JP | 0010000195 A | 1/1998 |

(56) References Cited

FOREIGN PATENT DOCUMENTS

| | | |
|---|---|---|
| JP | 10-155798 A | 6/1998 |
| JP | 11-070124 A | 3/1999 |
| JP | 11-169381 A | 6/1999 |
| JP | 11-192238 A | 7/1999 |
| JP | 11244298 A | 9/1999 |
| JP | 2000-102545 A | 4/2000 |
| JP | 2000342599 A | 12/2000 |
| JP | 2000350732 A | 12/2000 |
| JP | 2001008944 A | 1/2001 |
| JP | 2001029356 A | 2/2001 |
| JP | 2001-03400 | 4/2001 |
| JP | 2001128990 A | 5/2001 |
| JP | 2001-190564 A | 7/2001 |
| JP | 2002-136525 A | 5/2002 |
| JP | 2002-528166 A | 9/2002 |
| JP | 2003-175052 A | 6/2003 |
| JP | 2003245285 A | 9/2003 |
| JP | 2004-517668 A | 6/2004 |
| JP | 2004-528869 A | 9/2004 |
| JP | 2005-253789 A | 9/2005 |
| JP | 2006-015078 A | 1/2006 |
| JP | 2006-501939 A | 1/2006 |
| JP | 2006-095316 A | 4/2006 |
| JP | 2011125195 A | 6/2011 |
| SU | 401367 A1 | 10/1973 |
| WO | 0036986 A1 | 6/2000 |
| WO | 0059392 A1 | 10/2000 |
| WO | 0115614 A1 | 3/2001 |
| WO | 0154604 A1 | 8/2001 |
| WO | 02/45589 A2 | 6/2002 |
| WO | 2004/103156 A2 | 12/2004 |
| WO | 2006021269 A1 | 3/2006 |
| WO | 2005110264 A3 | 4/2006 |
| WO | 2007/103986 A2 | 9/2007 |
| WO | 2008040483 A1 | 4/2008 |
| WO | 2008/136837 A1 | 11/2008 |
| WO | 2012/044606 A2 | 4/2012 |

OTHER PUBLICATIONS

U.S. Appl. No. 13/072,945, Patrick L. Dumbauld.
U.S. Appl. No. 13/080,383, David M. Garrison.
U.S. Appl. No. 13/085,144, Keir Hart.
U.S. Appl. No. 13/091,331, Jeffrey R. Townsend.
U.S. Appl. No. 13/102,573, John R. Twomey.
U.S. Appl. No. 13/102,604, Paul E. Ourada.
U.S. Appl. No. 13/108,093, Boris Chernov.
U.S. Appl. No. 13/108,129, Boris Chernov.
U.S. Appl. No. 13/108,152, Boris Chernov.
U.S. Appl. No. 13/108,177, Boris Chernov.
U.S. Appl. No. 13/108,196, Boris Chernov.
U.S. Appl. No. 13/108,441, Boris Chernov.
U.S. Appl. No. 13/108,468, Boris Chernov.
U.S. Appl. No. 13/111,642, John R. Twomey.
U.S. Appl. No. 13/111,678, Nikolay Kharin.
U.S. Appl. No. 13/113,231, David M. Garrison.
U.S. Appl. No. 13/157,047, John R. Twomey.
U.S. Appl. No. 13/162,814, Barbara R. Tyrrell.
U.S. Appl. No. 13/166,477, Daniel A. Joseph.
U.S. Appl. No. 13/166,497, Daniel A. Joseph.
U.S. Appl. No. 13/179,919, Russell D. Hempstead.
U.S. Appl. No. 13/179,960, Boris Chernov.
U.S. Appl. No. 13/179,975, Grant T. Sims.
U.S. Appl. No. 13/180,018, Chase Collings.
U.S. Appl. No. 13/183,856, John R. Twomey.
U.S. Appl. No. 13/185,593, James D. Allen, IV.
U.S. Appl. No. 13/204,841, Edward J. Chojin.
U.S. Appl. No. 13/205,999, Jeffrey R. Unger.
U.S. Appl. No. 13/212,297, Allan J. Evans.
U.S. Appl. No. 13/212,308, Allan J. Evans.
U.S. Appl. No. 13/212,329, Allan J. Evans.
U.S. Appl. No. 13/212,343, Duane E. Kerr.
U.S. Appl. No. 13/223,521, John R. Twomey.
U.S. Appl. No. 13/227,220, James D. Allen, IV.
U.S. Appl. No. 13/228,742, Duane E. Kerr.
U.S. Appl. No. 13/231,643, Keir Hart.
U.S. Appl. No. 13/234,357 James D. Allen, IV.
U.S. Appl. No. 13/236,168, James D. Allen, IV.
U.S. Appl. No. 13/236,271, Monte S. Fry.
U.S. Appl. No. 13/243,628, William Ross Whitney.
U.S. Appl. No. 13/247,778, John R. Twomey.
U.S. Appl. No. 13/247,795, John R. Twomey.
U.S. Appl. No. 13/248,976, James D. Allen, IV.
U.S. Appl. No. 13/249,013, Jeffrey R. Unger.
U.S. Appl. No. 13/249,024, John R. Twomey.
U.S. Appl. No. 13/251,380, Duane E. Kerr.
U.S. Appl. No. 13/277,373 Glenn A. Homer.
U.S. Appl. No. 13/277,926, David M. Garrison.
U.S. Appl. No. 13/277,962, David M. Garrison.
Michael Choti, "Abdominoperineal Resection with the LigaSure Vessel Sealing System and LigaSure Atlas 20 cm Open Instrument" ; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps", Feb. 6, 1967, British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte,NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.

(56) References Cited

OTHER PUBLICATIONS

Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J. Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surge" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
U.S. Appl. No. 08/926,869, James G. Chandler.
U.S. Appl. No. 09/177,950, Randel A. Frazier.
U.S. Appl. No. 09/387,883, Dale F. Schmaltz.
U.S. Appl. No. 09/591,328, Thomas P. Ryan.
U.S. Appl. No. 12/336,970, Paul R. Sremcich.
U.S. Appl. No. 13/293,754, Jeffrey M. Roy.
U.S. Appl. No. 13/306,523, David M. Garrison.
U.S. Appl. No. 13/306,553, Duane E. Kerr.
U.S. Appl. No. 13/308,104, John R. Twomey.
U.S. Appl. No. 13/312,172, Robert J. Behnke, II.
U.S. Appl. No. 13/324,863, William H. Nau, Jr.
U.S. Appl. No. 13/344,729, James D. Allen, IV.
U.S. Appl. No. 13/355,829, John R.Twomey.
U.S. Appl. No. 13/357,979, David M. Garrison.
U.S. Appl. No. 13/358,136, James D. Allen, IV.
U.S. Appl. No. 13/360,925, James H. Orszulak.
U.S. Appl. No. 13/400,290, Eric R. Larson.
U.S. Appl. No. 13/404,435, Kim V. Brandt.
U.S. Appl. No. 13/404,476, Kim V. Brandt.
U.S. Appl. No. 13/412,879, David M. Garrison.
U.S. Appl. No. 13/412,897, Joanna Ackley.
U.S. Appl. No. 13/421,373, John R. Twomey.
U.S. Appl. No. 13/430,325, William H. Nau, Jr.
U.S. Appl. No. 13/433,924, Keir Hart.
U.S. Appl. No. 13/448,577, David M. Garrison.
U.S. Appl. No. 13/460,455, Luke Waaler.
U.S. Appl. No. 13/461,335, James D. Allen, IV.
U.S. Appl. No. 13/461,378, James D. Allen, IV.
U.S. Appl. No. 13/461,397, James R. Unger.
U.S. Appl. No. 13/461,410, James R. Twomey.
U.S. Appl. No. 13/464,569, Duane E. Kerr.
U.S. Appl. No. 13/466,274, Stephen M. Kendrick.
U.S. Appl. No. 13/467,767, Duane E. Kerr.
U.S. Appl. No. 13/470,543, Sean T. Dycus.
U.S. Appl. No. 13/470,775 James D. Allen, IV.
U.S. Appl. No. 13/470,797, John J. Kappus.
U.S. Appl. No. 13/482,589, Eric R. Larson.
U.S. Appl. No. 13/483,733, Dennis W. Butcher.
U.S. Appl. No. 13/488,093, Kristin D. Johnson.
U.S. Appl. No. 13/491,853, Jessica E. Olson.
U.S. Appl. No. 13/537,517, David N. Heard.
U.S. Appl. No. 13/537,577, Tony Moua.
U.S. Appl. No. 13/550,322, John J. Kappus.
U.S. Appl. No. 13/571,055, Paul Guerra.
U.S. Appl. No. 13/571,821, Joseph D. Bucciaglia.
U.S. Appl. No. 13/584,194, Sean T. Dycus.
European Search Report from corresponding application EP 12196678 dated May 10, 2013.

\* cited by examiner

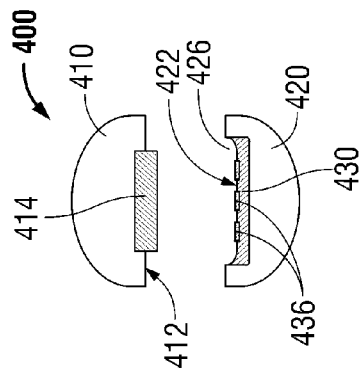
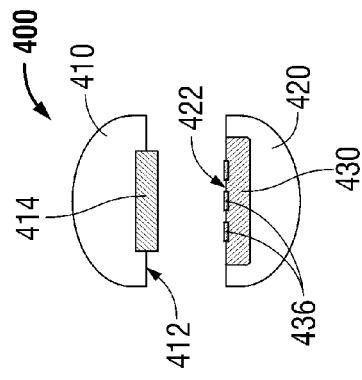
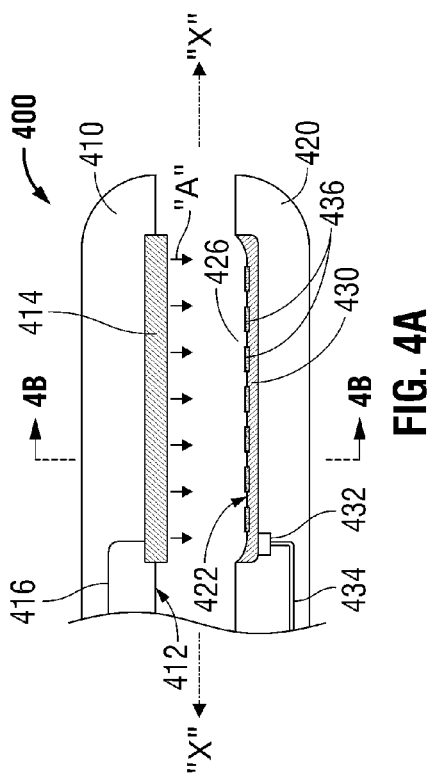
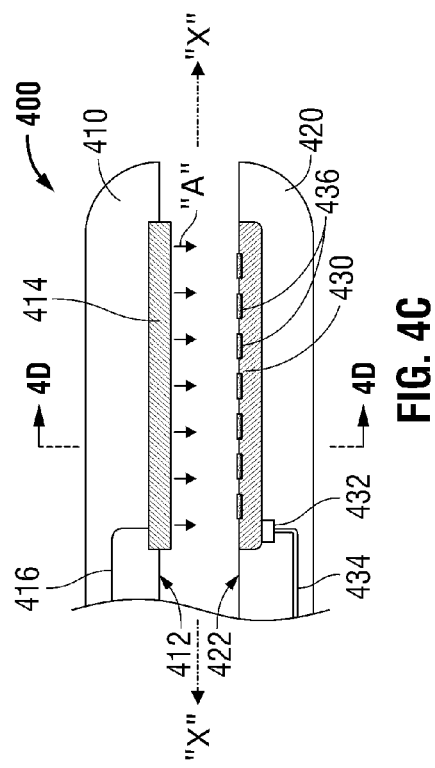

SURGICAL FORCEPS

CROSS-REFERENCE TO RELATED APPLICATIONS

This application is a continuation application of U.S. patent application Ser. No. 13/324,863, filed Dec. 13, 2011, the entire contents of which are incorporated herein by reference.

BACKGROUND

1. Technical Field

The present disclosure relates to surgical instruments and, more particularly, to surgical forceps for grasping, treating, and/or dividing tissue.

2. Description of Related Art

A forceps is a plier-like instrument which relies on mechanical action between its jaws to grasp, clamp and constrict vessels or tissue. Energy-based forceps utilize both mechanical clamping action and energy, e.g., RF energy, ultrasonic energy, microwave energy, thermal energy, light energy, etc., to affect hemostasis by heating tissue and blood vessels to coagulate and/or cauterize tissue. Certain surgical procedures require more than simply cauterizing tissue and rely on the unique combination of clamping pressure, precise energy control and/or gap distance (i.e., distance between opposing jaw members when closed about tissue) to "seal" tissue, vessels, and certain vascular bundles. Typically, once a vessel is sealed, the surgeon has to accurately sever the vessel along the newly formed tissue seal. Accordingly, many forceps have been designed which incorporate a knife or blade member that effectively severs the tissue along the tissue seal. Alternatively, or additionally, energy may be utilized to facilitate tissue division.

SUMMARY

As used herein, the term "distal" refers to that portion that is further from an operator while the term "proximal" refers to that portion that is closer to an operator. As used herein, the term "treat" refers to performing a surgical treatment to tissue using energy, e.g. heating, sealing, or energized cutting of tissue. As used herein, the term "energy" refers broadly to include all types of energy used to treat tissue, e.g., RF energy, ultrasonic energy, microwave energy, thermal energy, light energy, etc. As used herein, the term "light energy source" refers broadly to include all types of devices that produce light for medical use (e.g., tissue treatment). These devices include lasers, light emitting diodes (LEDs), lamps, and other accessories that produce light anywhere along an appropriate electromagnetic spectrum (e.g., from infrared to ultraviolet).

Any or all of the aspects described herein, to the extent they are consistent, may be used in conjunction with any of the other aspects described herein.

In accordance with one aspect of the present disclosure, a forceps is provided. The forceps includes an end effector assembly having first and second jaw members. One or both of the jaw members is movable relative to the other between a spaced-apart position, a first approximated position, and a second approximated position. In the first approximated position, the jaw members define a first gap distance "G" therebetween. In the second approximated position, the jaw members define a second gap distance "g" therebetween. One or both of the jaw members includes a first stop member coupled thereto and disposed between the jaw members. The first stop member is longitudinally translatable along a surface of the jaw member(s) from a first position, wherein the first stop member inhibits approximation of the jaw members beyond the first approximated position, and a second position, wherein the first stop member inhibits approximation of the jaw members beyond the second approximated position.

In one aspect, one of the jaw members includes the first stop member coupled thereto, while the other jaw member includes a second stop member fixedly disposed thereon. In this aspect, the second stop member is disposed between the jaw members in opposed relation relative to the first stop member.

In another aspect, the first and second stop members define opposed angled surfaces configured to mechanically interface with one another. The angled surfaces of the first and second stop members may be configured to mechanically interface with one another along only a portion of the angled surfaces in the first position, while being configured to mechanically interface with one another substantially along an entire length of the angled surfaces in the second position.

In yet another aspect, one or both of the jaw members is adapted to connect to a source of light energy for treating tissue grasped between the jaw members.

In still another aspect, the first stop member is coupled to a motor that is configured to translate the first stop member between the first and second positions.

A forceps provided in accordance with another aspect of the present disclosure includes an end effector assembly having first and second jaw members. Each of the jaw members defining an opposed tissue contacting surface. One or both of the jaw members is movable relative to the other between a spaced-apart position and an approximated position for grasping tissue therebetween. One or both of the jaw members includes a tensioning mechanism disposed within a cavity defined therein. The tensioning mechanism includes a belt supported thereon. A segment of the belt defines at least a portion of the tissue contacting surface of the jaw member. The tensioning mechanism is transitionable between a generally un-tensioned state, wherein the segment of the belt is relatively less tensioned, and a tensioned state, wherein the segment of the belt is relatively more tensioned.

In one aspect, the belt is rotatably supported about a plurality of rollers. One or more of the rollers may be movable relative to the other rollers between a first position and a second position to transition the tensioning mechanism between the generally un-tensioned state and the tensioned state. Further, in some aspects, a motor is provided for moving the one or more rollers between the first and second positions.

In another aspect, one or both of the jaw members is adapted to connect to a source of light energy for treating tissue grasped between the jaw members.

In still another aspect, the belt is formed partially or entirely from a transparent material to permit passage of light energy therethrough.

A forceps provided in accordance with another aspect of the present disclosure includes an end effector assembly having first and second jaw members, each of which defines an opposed tissue contacting surface. One or both of the jaw members is movable relative to the other between a spaced-apart position and an approximated position for grasping tissue therebetween. One or both of the jaw members includes an inflatable member disposed within a cavity defined therein. The inflatable member includes an outer surface defining at least a portion of the tissue contacting surface of the jaw member. The inflatable member is transitionable between a generally deflated state, wherein the inflatable member occupies only a portion of the cavity, and an inflated state, wherein the inflatable member substantially occupies the entire cavity.

In one aspect, fluid is selectively supplied to the inflatable member to transition the inflatable member from the generally deflated state to the inflated state.

In another aspect, one or more relief valves is disposed on the outer surface of the inflatable member. The relief valve(s) is configured to permit fluid to exit the inflatable member to maintain a pressure of the inflatable member below a pre-determined pressure.

In yet another aspect, the fluid exiting the inflatable member via the relief valve(s) is configured for one or more of: cooling tissue, cooling the jaw members, facilitating treatment of tissue, inhibiting tissue from sticking to the jaw member, and cleaning the jaw members.

In still another aspect, one or both of the jaw members is adapted to connect to a source of light energy for treating tissue grasped between the jaw members.

In another embodiment, the inflatable member includes a pre-determined volume of fluid disposed therein. The pre-determined volume of fluid is configured to undergo a phase-change upon heating to a pre-determined temperature to transition the inflatable member from the generally deflated state to the inflated state.

BRIEF DESCRIPTION OF THE DRAWINGS

Various aspects of the present disclosure are described herein with reference to the drawings wherein like reference numerals identify similar or identical elements:

FIG. 4A is an enlarged, longitudinal cross-sectional view of another embodiment of an end effector assembly provided in accordance with the present disclosure, wherein the end effector assembly includes an inflatable member disposed within one of the jaw members, the inflatable member disposed in a generally deflated state;

FIG. 4B is an enlarged, transverse cross-sectional view taken along section line 4B-4B of FIG. 4A;

FIG. 4C is an enlarged, longitudinal cross-sectional view of the end effector assembly of FIG. 4A, wherein the inflatable member is disposed in an inflated state;

FIG. 4D is an enlarged, transverse cross-sectional view taken along section line 4D-4D of FIG. 4C;

DETAILED DESCRIPTION

The present disclosure relates generally to apparatus, systems and methods for treating tissue, e.g., heating, sealing and/or dividing tissue using energy. The present disclosure is particularly advantageous for treating tissue using light energy, although the present disclosure is equally applicable for use with various other forms of energy, e.g., RF energy, ultrasonic energy, microwave energy, thermal energy, etc. However, while different considerations may apply depending on the particular form of energy used, the novel aspects of the present disclosure remain generally consistent regardless of the form of energy used. For simplicity and consistency purposes, the various aspects of the present disclosure will be described hereinbelow with respect to treating tissue using light energy.

Figure 1A:
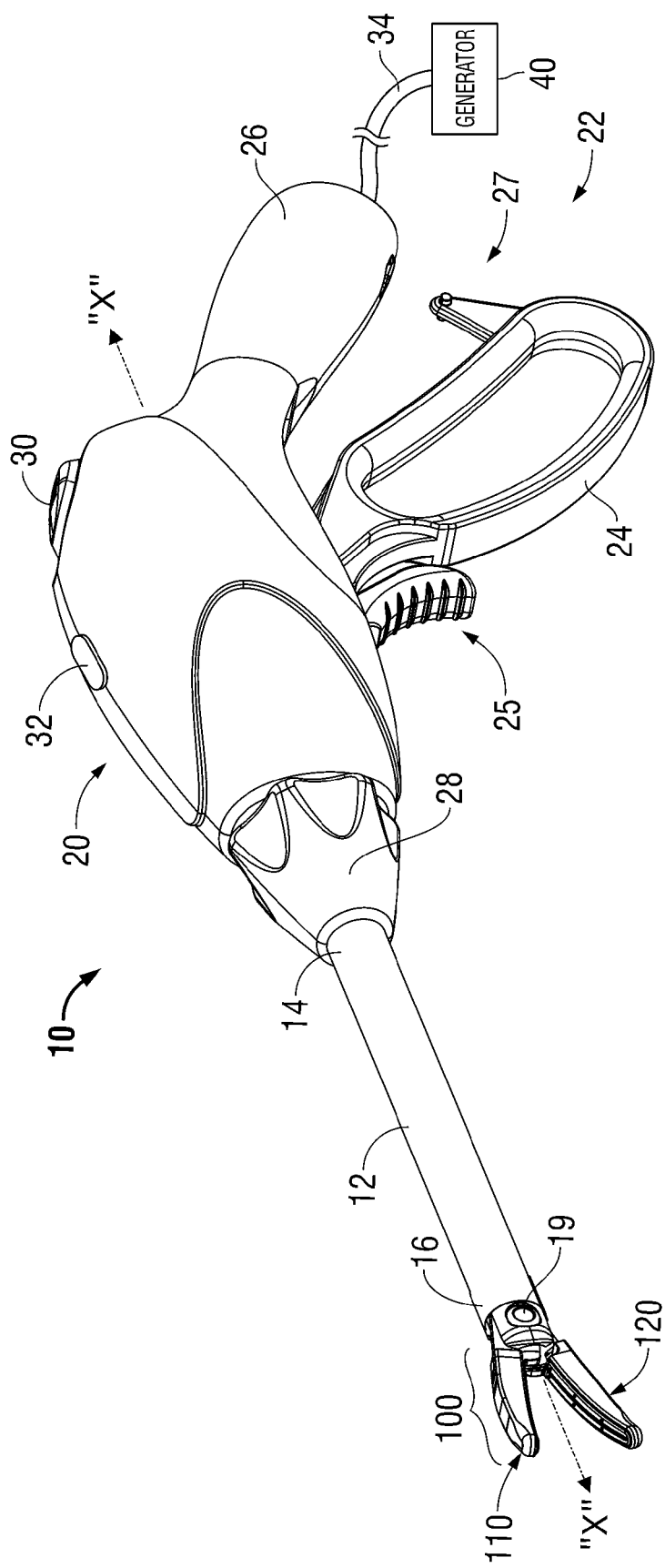
FIG. 1A is a perspective view of one embodiment of an endoscopic forceps provided in accordance with the present disclosure.
Figure 1B:
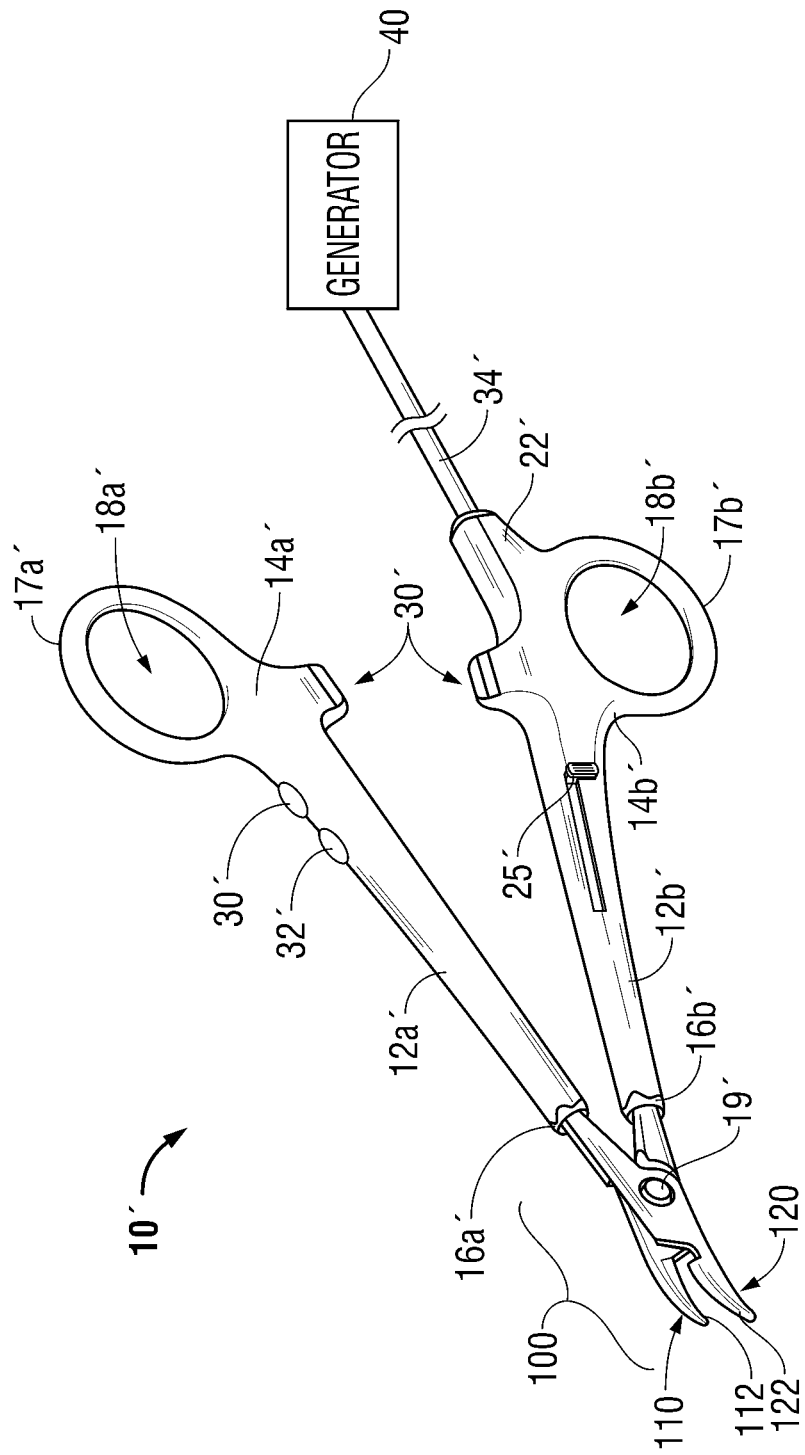
FIG. 1B is a perspective view of one embodiment of an open forceps provided in accordance with the present disclosure.

Referring to FIGS. 1A and 1B, FIG. 1A depicts an endoscopic surgical forceps 10 configured for use in connection with endoscopic surgical procedures, while FIG. 1B depicts an open surgical forceps 10' configured for use in connection with traditional open surgical procedures. For the purposes herein, either an endoscopic instrument, e.g., forceps 10, an open instrument, e.g., forceps 10', or any other suitable surgical instrument may be utilized in accordance with the present disclosure. Obviously, different connections and considerations apply to each particular type of instrument; however, the novel aspects with respect to the end effector assembly and its operating characteristics remain generally consistent with respect to both open and endoscopic configurations.

Turning to FIG. 1A, forceps 10 defines a longitudinal axis "X-X" and includes a shaft 12, a housing 20, a handle assembly 22, a trigger assembly 25, a rotating assembly 28, and an end effector assembly 100. Shaft 12 has a distal end 16 configured to mechanically engage end effector assembly 100 and a proximal end 14 that mechanically engages housing 20. A cable 34 couples forceps 10 to a light energy source, e.g., generator 40, for transmitting light energy and control signals between the light energy source and forceps 10. Generator 40 generates light energy adapted to treat tissue and may also be configured to generate various other forms of energy. In particular, generator 40 may be configured to output laser light energy having a wavelength from about 200 nm to about 11,000 nm. Alternatively or additionally, generator 40 may be configured to produce various other forms of energy, e.g., RF energy, ultrasonic energy, etc., for treating tissue, providing power to forceps 10, and/or other functions. Cable 34 is internally divided within handle assembly 22 and shaft 12 to transmit light energy and/or other forms of energy through various paths and ultimately to end effector assembly 100.

With continued reference to FIG. 1, handle assembly 22 includes a movable handle 24 and a fixed handle 26. Fixed handle 26 is integrally associated with housing 20 and movable handle 24 is movable relative to fixed handle 26. Movable handle 24 is ultimately connected to a drive assembly (not shown) that, together, mechanically cooperate to impart movement of jaw members 110, 120 of end effector assembly 100 between a spaced-apart position and an approximated position to grasp tissue therebetween. As shown in FIG. 1, movable handle 24 is initially spaced-apart from fixed handle 26 and, correspondingly, jaw members 110, 120 are disposed in the spaced-apart position. Movable handle 24 is movable from this initial position to one or more compressed positions corresponding to one or more approximated positions of jaw members 110, 120. A latching assembly 27 may be provided for selectively locking movable handle 24 relative to fixed handle 26 at various positions between the initial position and the compressed position(s) to lock jaw members 110, 120 at various different positions during pivoting, e.g., the one or more approximated positions. Rotating assembly 28 is rotatable in either direction about a longitudinal axis "X-X" to rotate end effector 100 about longitudinal axis "X-X."

End effector assembly 100 is shown attached at a distal end 16 of shaft 12 and includes a pair of opposing jaw members 110 and 120. Each jaw member 110, 120 includes a tissue contacting surface 112, 122, respectively, disposed on an opposed surface thereof. Tissue contacting surfaces 112, 122 cooperate to grasp and seal tissue held therebetween upon application of energy from generator 40. Tissue contacting surfaces 112, 122 are ultimately connected to generator 40 and configured to transmit light energy through tissue grasped therebetween.

End effector assembly 100 is designed as a bilateral assembly, i.e., where both jaw member 110 and jaw member 120 are movable about a pivot 19 relative to one another and to shaft 12. However, end effector assembly 100 may alternatively be configured as a unilateral assembly, i.e., where one of the jaw members, e.g., jaw member 120, is fixed relative to shaft 12 and the other jaw member, e.g., jaw member 110, is movable about pivot 19 relative to shaft 12 and the fixed jaw member 110, 120.

In some embodiments, a knife assembly (not shown) is disposed within shaft 12 and a knife channel (not shown) is defined within one or both jaw members 110, 120 to permit reciprocation of a knife blade (not shown) therethrough, e.g., via actuation of trigger assembly 25, to cut tissue grasped between jaw members 110, 120. Alternatively or additionally, end effector assembly 100 may be configured for energy-based tissue cutting.

Continuing with reference to FIG. 1A, first and second switch assemblies 30 and 32 disposed on housing 20 are selectively activatable to provide light energy from generator 40 to tissue contacting surface 112 of jaw member 110 (and/or tissue contacting surface 122 of jaw member 120) of end effector assembly 100. More particularly, first switch assembly 30 may be configured to supply light energy to end effector assembly 100 for a first mode of operation, while second switch assembly 32 may be configured to supply light energy (or a different form of energy) to end effector assembly 100 for a second mode of operation. Although two switch assemblies 30, 32 are shown, forceps 10 may alternatively include greater or fewer than two switch assemblies 30, 32 for performing various different tissue treatment procedures and/or for operating end effector assembly 100 in various different modes.

Referring to FIG. 1B, an open forceps 10' is shown including two elongated shafts 12a' and 12b', each having a proximal end 14a' and 14b', and a distal end 16a' and 16b', respectively. Similar to forceps 10 (FIG. 1A), forceps 10' is configured for use with end effector assembly 100. More specifically, end effector assembly 100 is attached to distal ends 16a' and 16b' of shafts 12a' and 12b', respectively. As mentioned above, end effector assembly 100 includes a pair of opposing jaw members 110 and 120 that are pivotably connected about a pivot 19'. Each shaft 12a' and 12b' includes a handle 17a' and 17b' disposed at the proximal end 14a' and 14b' thereof. Each handle 17a' and 17b' defines a finger hole 18a' and 18b' therethrough for receiving a finger of the user. As can be appreciated, finger holes 18a' and 18b' facilitate movement of the shafts 12a' and 12b' relative to one another that, in turn, pivots jaw members 110 and 120 from an open position, wherein the jaw members 110 and 120 are disposed in spaced-apart relation relative to one another, to a closed position, wherein jaw members 110 and 120 cooperate to grasp tissue therebetween.

A ratchet 30' may be included for selectively locking the jaw members 110 and 120 relative to one another at various positions during pivoting. Ratchet 30' may include graduations or other visual markings that enable the user to easily and quickly ascertain and control the amount of closure force desired between the jaw members 110 and 120.

With continued reference to FIG. 1B, one of the shafts, e.g., shaft 12b', includes a proximal shaft connector 22' that is designed to connect the forceps 10' to a source of energy such as generator 40. Proximal shaft connector 22' secures cable 34' to forceps 10' such that the user may selectively apply energy to tissue contacting surfaces 112, 122 of jaw members 110, 120, respectively, similarly as described above with respect to forceps 10 (FIG. 1A).

One or both of the shafts, e.g., shaft 12a', may include first and second switch assemblies 30', 32', respectively, although greater or fewer than two switch assemblies 30', 32' may also be provided. Switch assemblies 30', 32' are configured to selectively provide energy to end effector assembly 100 in one or modes of operation. One or both of the shafts, e.g., shaft 12b', may further include a trigger assembly 25' for selectively providing energy in another mode of operation and/or for reciprocating a knife blade (not shown) between jaw members 110, 120.

Figure 1C:
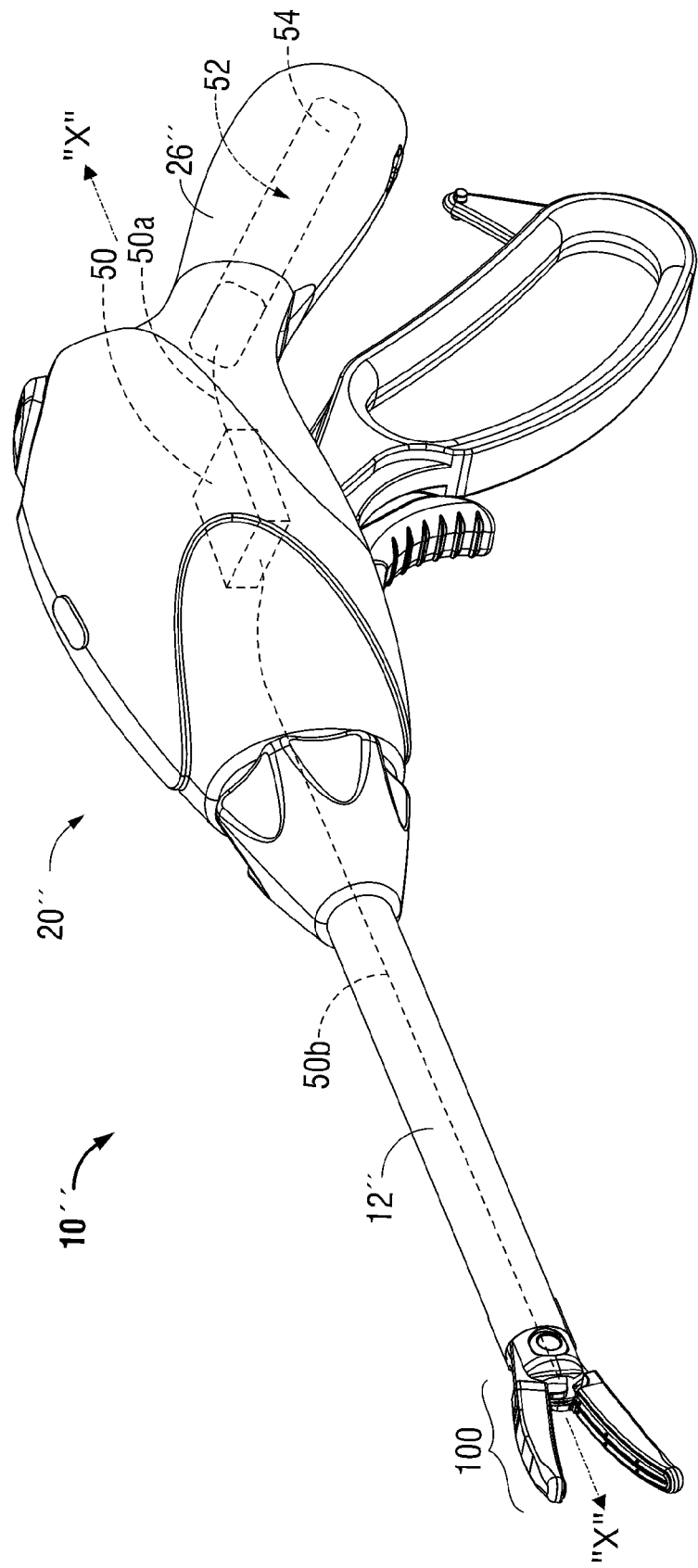
FIG. 1C is a perspective view of another embodiment of an endoscopic forceps provided in accordance with the present disclosure.

Referring to FIG. 1C, a cordless, or portable forceps 10" is shown including an internal energy source 50, e.g., for generating light energy and/or other forms of energy, disposed within housing 20". Internal energy source 50 is operably coupled to a battery compartment 52 disposed within fixed handle 26" via one or more wires 50a. Battery compartment 52 is adapted to receive one or more batteries 54 for providing suitable energy to internal energy source 50. Internal energy source 50 provides energy to end effector assembly 100 via one or more fibers 50b (or any other suitable transmission medium, e.g., wires, cables, etc.) that extend through shaft 12". Forceps 10" may otherwise be configured similar to forceps 10 (FIG. 1A), discussed above.

Various end effector assemblies configured for use with forceps 10, 10', 10", or any other suitable surgical instrument adapted to operably engage an end effector assembly, are described in detail hereinbelow with reference to FIGS. 2A-5F. In particular, end effector assemblies 200, 300, 400 and 500 (FIGS. 2A-2C, 3A-3C, 4A-4D and 5A-5F, respectively) each include features that are configured to vary the pressure exerted on tissue grasped between the jaw members thereof while treating tissue in order to facilitate sealing and/or cutting of tissue. As will be described below, such a feature is particularly advantageous with respect to tissue treatment using light energy. However, the present disclosure is equally applicable for treating tissue using other forms of energy.

Light energy is suitable for sealing tissue since it is converted into heat energy by absorption at a molecular level. That is, light energy at optical wavelengths (e.g., from about 200 nm to about 11,000 nm) is used to heat tissue due to absorption of light energy at these wavelengths. However, optical properties of tissue are known to change during heating. For example, properties such as the absorption coefficient ($\mu_a$), scattering coefficient ($\mu_s$), and anisotropy coefficient (g) have been shown to change as a function of temperature and time. These properties, in turn, affect the transmission and reflection of light as it interacts with tissue.

It has been found that, due to the above, varying the pressure exerted on tissue during the application of light energy to tissue facilitates the formation of a tissue seal and/or the division of tissue along the tissue seal. More specifically, it has been found that initially applying a relatively smaller pressure to tissue allows for maximum absorption of light energy by tissue and that, once tissue has absorbed a sufficient amount of energy, i.e., once tissue has been sufficiently heated, increasing the pressure applied to tissue facilitates formation of the tissue seal. Further, it has also been found that increasing the pressure applied to tissue, e.g., after formation of a tissue seal, facilitates the cutting of tissue using light energy. End effector assemblies 200, 300, 400 and 500 (FIGS. 2A-2C, 3A-3C, 4A-4D and 5A-5F, respectively), each of which will be described in detail in turn below, implement these advantageous findings by providing features that are configured to vary the pressure exerted on tissue grasped between the jaw members thereof during the application of light energy to tissue in order to facilitate sealing and/or cutting of tissue.

Figure 2A:
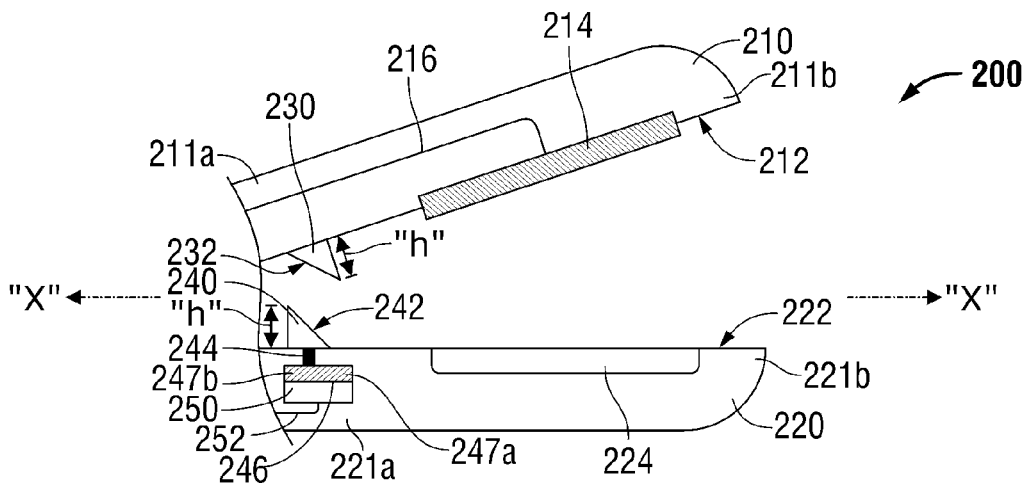
FIG. 2A is an enlarged, longitudinal cross-sectional view of one embodiment of an end effector assembly provided in accordance with the present disclosure, wherein jaw members of the end effector assembly are disposed in a spaced-apart position.
Figure 2B:
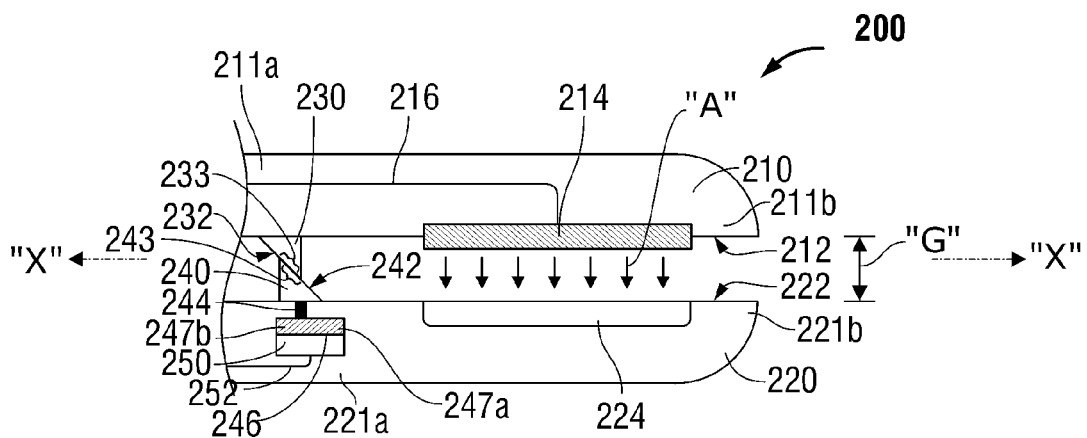
FIG. 2B is an enlarged, longitudinal cross-sectional view of the end effector assembly of FIG. 2A, wherein the jaw members are disposed in a first approximated position.
Figure 2C:
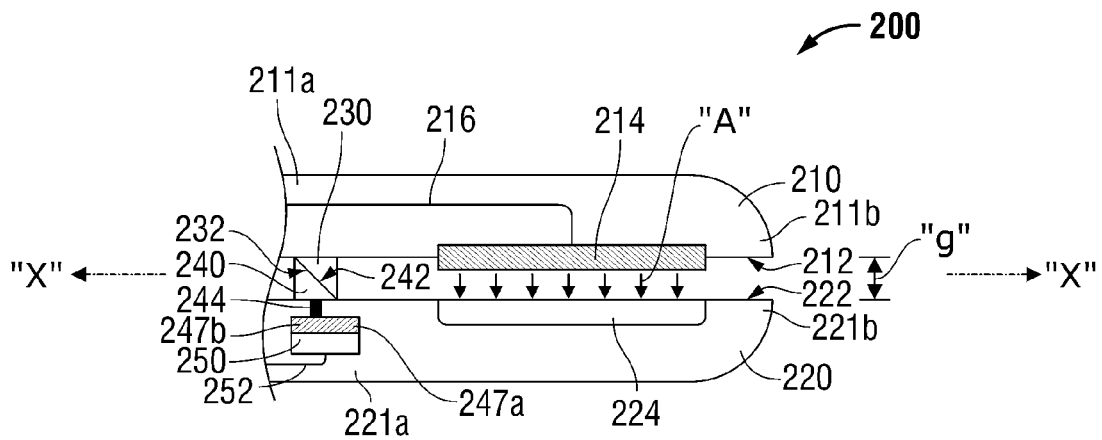
FIG. 2C is an enlarged, longitudinal cross-sectional view of the end effector assembly of FIG. 2A, wherein the jaw members are disposed in a second approximated position.

With reference to FIGS. 2A-2C, one embodiment of an end effector assembly 200 is shown defining a longitudinal axis "X-X" and generally includes first and second jaw members 210, 220, respectively, that are movable relative to one another between a spaced-apart position (FIG. 2A), a first approximated position (FIG. 2B), and a second approximated position (FIG. 2C). Each jaw member 210, 220 of end effector assembly 200, similar to end effector assembly 100 (FIGS. 1A-1C), includes an opposed surface 212, 222, respectively. Jaw members 210, 220 define proximal ends 211a, 221a, respectively, and distal ends 211b, 221b, respectively.

One or both of the jaw members, e.g., jaw member 210, includes a tissue contacting member 214 disposed on or along surface 212 that is configured to facilitate the transmission of light energy from the light energy source, e.g., generator 40 (FIG. 1A) or internal energy source 50 (FIG. 1C), to tissue grasped between jaw members 210, 220. More specifically, cable 216 couples tissue contacting member 214 of jaw member 210 to the light energy source such that light energy may be transmitted between jaw members 210, 220, as indicated by arrows "A" and through tissue grasped therebetween. The other jaw member, e.g., jaw member 220, includes a tissue contacting member 224 disposed on or along surface 222 that is configured to receive, absorb, or reflect the light energy transmitted from jaw member 210 and through tissue.

Continuing with reference to FIGS. 2A-2C, jaw member 210 includes a stop member 230 disposed on surface 212 thereof towards proximal end 211a thereof. Stop member 230 defines a height "h" and includes an angled surface 232 oriented in a generally proximally-facing direction, although other configurations may also be provided. Stop member 230 is positioned proximally of tissue contacting member 214 so as not to interfere with the grasping of tissue and/or transmission of energy between tissue contacting members 214, 224 of jaw members 210, 220, respectively.

Jaw member 220 likewise includes a stop member 240 disposed on surface 222 thereof towards proximal end 221a thereof. Stop member 240 defines a height "h" and includes an angled surface 242 oriented in a generally distally-facing direction (although other configurations may also be provided) such that angled surface 242 of stop member 240 opposes angled surface 232 of stop member 230. Stop member 240 is positioned proximally of tissue contacting member 224 so as not to interfere with the grasping of tissue and/or transmission of energy between tissue contacting members 214, 224 of jaw members 210, 220, respectively, and such that stop members 230, 240 of jaw members 210, 220, respectively, generally oppose one another.

One of the stop members, e.g., stop member 240, is longitudinally translatable along the respective jaw member thereof, e.g., jaw member 220, between a distal position (FIG. 2B) and a proximal position (FIG. 2C). The other stop member, e.g., stop member 230, is fixed in position relative to the respect jaw member thereof, e.g., jaw member 210. However, this configuration may be reversed, e.g., wherein stop member 240 is fixed and stop member 230 is translatable along jaw member 210, or both stop members 230, 240, may be configured to translate along the respective jaw member 210, 220 thereof.

Stop member 240, as mentioned above, is selectively translatable along jaw member 220 between a distal position (FIG. 2B) and a proximal position (FIG. 2C). More specifically, stop member 204 is mounted on a post 244 that is engaged within a track 246 such that, upon movement of post 244 along track 246 from distal end 247a to proximal end 247b thereof, stop member 240 is moved from the distal position (FIG. 2B) to the proximal position (FIG. 2C). A powered motor 250 coupled to post 244 and track 246 may be provided for translating post 244 along track 246 to thereby move stop member 240 between the distal and proximal positions. A cable 252 couples powered motor 250 to the energy source, e.g., generator 40 (FIG. 1A) or internal energy source 50 (FIG. 1C), for providing power to motor 250. Motor 250 may be actuated manually, e.g., via squeezing movable handle 24, activating one or more of switch assemblies 30, 32 or trigger assembly 25 (see FIG. 1A), or via any other suitable mechanism. Alternatively, motor 250 may be automatically actuated, e.g., via one or more sensors (not explicitly shown) configured to sense the properties of jaw members 210, 220 and/or tissue. However, although motor 250 may be actuated manually, motor 250 is configured to automatically translate stop member 240 according to a pre-determined function, e.g., at a pre-determined rate (variable or constant rate), at pre-determined intervals, upon sensing a particular condition, etc., thus eliminating the inaccuracies associated with manually-controlled movement of stop member 240.

As an alternative to motor 250, post 244 may be spring-driven, pneumatically or hydraulically driven, e.g., via a solenoid, driven by a shape-memory material, driven by the phase-change of a material, or may otherwise be driven to translate along track 246 between the distal and proximal ends 247a, 247b, respectively, thereof according to one or more pre-determined functions. For example, a shape memory material may be coupled between post 244 and a jaw member 220 such that, upon heating of the shape memory material from its martensite temperature ($A_s$) to its austenite temperature ($A_f$), the shape memory material change from its "cold" shape to its "hot" shape, thereby driving, e.g., pushing or pulling, post 244 to translate along track 246.

It is also contemplated that the stop members 230 and 240 and the components associated therewith be positioned proximally of the pivot (not shown) coupling jaw members 210, 220, for similar purposes as described above.

With continued reference to FIGS. 2A-2C, the operation of end effector assembly 200 is described. Initially, as shown in FIG. 2A, jaw members 210, 220 are disposed in the spaced-apart position and stop member 240 is disposed in the distal position wherein post 244 is disposed at distal end 247a of track 246. In this position, end effector assembly 200 may be manipulated and/or maneuvered into position such that tissue to be treated, e.g., sealed and/or cut, is disposed between jaw members 210, 220.

Next, with jaw members 210, 220 in position, movable handle 24 (FIG. 1A) is squeezed towards fixed handle 26 (FIG. 1A), or jaw members 210, 220 are otherwise moved relative to one another, such that jaw members 210, 220 are pivoted relative to one another from the spaced-apart position (FIG. 2A) to the first approximated position (FIG. 2B) to grasp tissue therebetween. As jaw members 210, 220 are approximated relative to one another, stop member 240 of jaw member 220, which, at this point, remains disposed in the distal position, contacts stop member 230 of jaw member 210 to inhibit further approximation of jaw members 210, 220, thus defining the first approximated position of jaw members 210, 220 shown in FIG. 2B. More specifically, as the first approximated position is achieved, angled surfaces 232, 242 of stop members 230, 240, respectively, are urged into mating contact, mechanically interfacing with one another along a portion 233, 243 of the surfaces 232, 242, respectively, thereof to inhibit further approximation of jaw members 210, 220. This is due to the angled configuration of angled surfaces 232, 242 of stop members 230, 240, respectively, and the fixed longitudinal positioning (at this point) of stop members 230, 240 relative to one another.

With jaw members 210, 220 disposed in the first approximated position, as shown in FIG. 2B, a first, relatively large gap distance "G" is defined between surfaces 212, 222 of jaw members 210, 220, respectively, (or tissue contacting members 214, 224 thereof) and, as a result of this relatively larger gap distance "G" between jaw members 210, 220, a relatively smaller pressure is applied to tissue grasped therebetween. As will be described below, upon longitudinal translation of stop member 240 relative to stop member 230 from the distal position (FIG. 2B) to the proximal position (FIG. 2C), jaw members 210, 220 are permitted to further approximate relative to one another to the second approximated position (FIG. 2C), wherein a greater pressure is applied to tissue grasped between jaw members 210, 220.

Continuing with reference to FIG. 2B, with jaw members 210, 220 disposed in the first approximated position and grasping tissue between surfaces 212, 222, respectively, thereof (or tissue contacting members 214, 224 thereof), energy may be transmitted from tissue contacting member 214 of jaw member 210, through tissue, to tissue contacting member 224 of jaw member 220, as indicated by arrows "A" (although energy may alternatively be transmitted between tissue contacting members 214, 224 in either or both directions). Activation of the energy may be effected via actuating one or more of first and second switch assemblies 30 and 32 (FIG. 1A). As mentioned above, with jaw members 210, 220 disposed in the first approximated position defining first gap distance "G" therebetween, a relatively smaller pressure is applied to tissue, thus allowing for maximum absorption of light energy by tissue at the beginning of the sealing cycle.

Once tissue has absorbed a sufficient amount of energy, upon satisfaction of a pre-determined condition, time, and/or function, or upon manual or other suitable automatic actuation, motor 250 (or any other suitable mechanism configured to translate stop member 240) is activated to translate post 244 translated along track 246 from the distal end 247a thereof towards the proximal end 247b thereof. Motor 250 may be configured to translate post 244 at a constant or variable rate, and/or either continuously or incrementally such that stop member 240 is translated from the more distal position towards the more proximal position in accordance with a pre-determined function (or functions).

Referring to FIG. 2C, as motor 250 translates post 244 and, thus, stop member 240 proximally, jaw members 210, 220 are permitted to approximate further relative to one another. More specifically, as stop member 240 is translated proximally, angled surface 242 of stop member 240 no longer inhibits further approximation of jaw members 210, 220 but, rather, permits angled surfaces 232, 242 of stop members 230, 240, respectively, to slide along one another, allowing jaw members 210, 220 to approximate further relative to one another. With stop members 230, 240 no longer blocking further approximation of jaw members 210, 220, jaw members 210, 220 may be moved to the second approximated position, e.g., via manually squeezing movable handle 24 (FIG. 1A) further towards fixed handle 26 (FIG. 1A), or via any other suitable mechanism.

With jaw members 210, 220 disposed in the second approximated position, as shown in FIG. 2C, a second gap distance "g" that is smaller than first gap distance "G" is defined between surfaces 212, 222 of jaw members 210, 220, respectively, (or tissue contacting members 214, 224 thereof) and, as a result, a relatively larger pressure is applied to tissue grasped therebetween. In this second approximated position, angled surfaces 232, 242 of stop members 230, 240, respectively, mate or mechanically interface with one another substantially along length of the surfaces 232, 242, such that the second gap distance "g" defines the minimum gap distance between jaw members 210, 220, which is approximately equal to the height "h" of stop members 230, 240. Alternatively or additionally, motor 250 may be configured to translate stop member 240 incrementally, thereby defining one or more intermediate approximated positions between the first and second approximated positions. As can be appreciated, these intermediate approximated positions would define gap distanced between jaw members 210, 220 between first gap distance "G" and second gap distance "g" would exert pressures on tissue between the relatively smaller pressure associated with first gap distance "G" and the relatively larger pressure associated with second gap distance "g."

Continuing with reference to FIG. 2C, with jaw members 210, 220 disposed in the second approximated position and grasping tissue between surfaces 212, 222, respectively, thereof (or tissue contacting members 214, 224 thereof) at an increased pressure, the transmission of energy from tissue contacting member 214 of jaw member 210, through tissue, to tissue contacting member 224 of jaw member 220 may be continued to complete formation of a tissue seal and/or to divide tissue along the previously formed tissue seal. Alternatively, jaw members 210, 220 may be moved to an intermediate approximated position for completion of the tissue seal, and may then be moved to the second approximated position for cutting tissue along the previously formed tissue seal. At the completion of tissue treatment, e.g., sealing and/or cutting of tissue, jaw members 210, 220 are returned to the spaced-apart position and end effector assembly 200 is removed from the surgical site (or is repositioned adjacent other tissue to be treated).

Figure 3A:
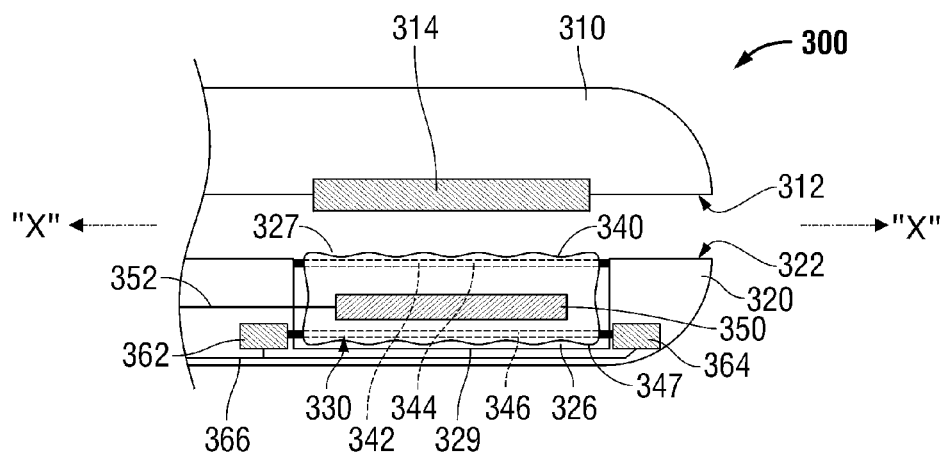
FIG. 3A is an enlarged, longitudinal cross-sectional view of another embodiment of an end effector assembly provided in accordance with the present disclosure, wherein the end effector assembly includes a tensioning mechanism disposed within one of the jaw members.
Figure 3B:
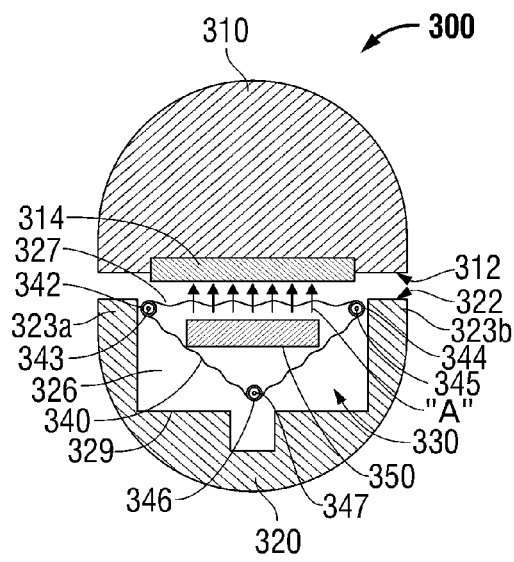
FIG. 3B is an enlarged, transverse cross-sectional view of the end effector assembly of FIG. 3A, wherein the tensioning mechanism is disposed in a generally un-tensioned state.
Figure 3C:
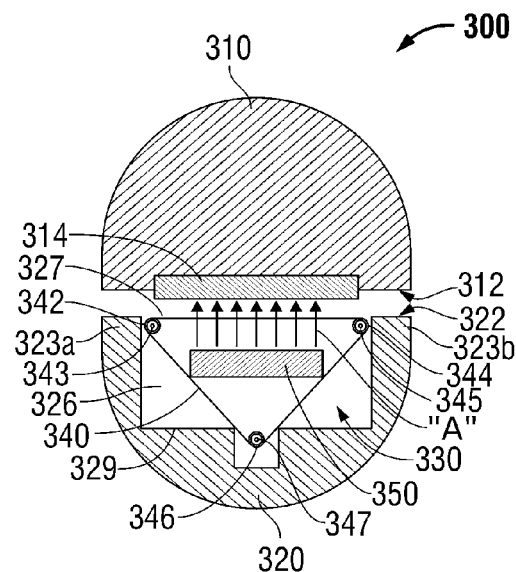
FIG. 3C is an enlarged, transverse cross-sectional view of the end effector assembly of FIG. 3A, wherein the tensioning mechanism is disposed in a tensioned state.

Referring to FIGS. 3A-3C, another embodiment of an end effector assembly 300 is shown defining a longitudinal axis "X-X" and generally including first and second jaw members 310, 320, respectively, that are movable relative to one another between a spaced-apart position and an approximated position (FIGS. 3A-3C) for grasping tissue therebetween.

One of the jaw members, e.g., jaw member 310, includes a tissue contacting member 314 disposed on or along surface 312 thereof that is configured to facilitate the transmission of light energy from the light energy source, e.g., generator 40 (FIG. 1A) or internal energy source 50 (FIG. 1C), to tissue grasped between jaw members 310, 320. That is, tissue contacting member 314 of jaw member 310 may be coupled to the light energy source such that light energy may be transmitted from jaw member 310, through tissue grasped between jaw members 310, 320, and to jaw member 320. Alternatively, tissue contacting member 314 may be configured to receive light energy, e.g., absorb or reflect light energy, in embodiments where light energy is transmitted from jaw member 320 towards jaw member 310.

The other jaw member (or both jaw members), e.g., jaw member 320, includes a tensioning mechanism 330 disposed within a cavity 326 defined within jaw member 320. Tensioning mechanism 330 includes a belt 340 disposed about first, second, and third rollers 342, 344, 346, respectively. More specifically, first and second rollers 342, 344, respectively, are positioned adjacent open end 327 of cavity 326 defined within jaw member 320, while third roller 346 is positioned adjacent bottom surface 329 defining cavity 326 such that tensioning mechanism 330 defined a generally triangular-shaped cross-sectional configuration. Although tensioning mechanism 330 is shown including three rollers 342, 344, 346 and defining a triangular-shaped cross-sectional configurations, other configurations and/or greater or fewer rollers may also be provided.

Belt 340 and rollers 342, 344, 346 of tensioning mechanism 330 are configured such that, as best shown in FIGS. 3B and 3C, a portion of belt 340 extends across open end 327 of cavity 326 to define a tissue contacting surface 322 opposing tissue contacting member 314 of jaw member 310. More specifically, first and second rollers 342, 344 are rotatably supported on first and second spaced-apart support bars 343, 345, respectively, disposed on opposite sides 323a, 323b jaw member 320. Each of the first and second support bars 343, 345 extends longitudinally along open end 327 of cavity 326 and is engaged within jaw member 320 at each end thereof. Thus, the portion of belt 340 extending between first and second rollers 342, 344, respectively, defines at least a portion of tissue contacting surface 322 of jaw members 320. Third roller 346, on the other hand, is rotatably supported on a third support bar 347 that is transversely centered within cavity 326 towards the bottom surface 329 thereof. Third support bar 347 is coupled to one or more powered motors 362, 364. Motors 362, 364, as will be described in greater detail below, work in cooperation with one another to raise and lower third support bar 347 and, thus, third roller 346 between a raised position (FIG. 3B) corresponding to a generally un-tensioned state of tensioning mechanism 330 and a lowered position (FIG. 3C) corresponding to a tensioned state of tensioning mechanism 330. Alternatively or additionally, tensioning mechanism 330 may be transitioned between the generally un-tensioned state and the tensioned state by translating first and/or second rollers 342, 344, respectively, or via powered rotation of one or more of rollers 342, 344, 346.

Continuing with reference to FIGS. 3A-3C, belt 340 may be formed at least partially from a transparent material to permit transmission of light energy therethrough. As such, jaw member 320 may include a energy transmission member 350 positioned within cavity 326 below the portion of belt 340 forming tissue contacting surface 322. Energy transmission member 350 is coupled to the light energy source, e.g., generator 40 (FIG. 1A) or internal energy source 50 (FIG. 1C), via cable 352 such that light energy may be transmitted from energy transmission member 350 of jaw member 320, through belt 340, through tissue grasped between jaw members 310, 320, and to jaw member 310, as indicated by arrows "A." Alternatively, belt 340 and/or energy transmission member 350 may be configured to receive light energy, e.g., absorb or reflect light energy, in embodiments where light energy is transmitted from jaw member 310 towards jaw member 320. In some embodiments, belt 340 is formed at least partially from a flexible material to provide tissue contacting surface 322 with some degree of resiliency.

Third roller 346, as mentioned above, is coupled to motors 362, 364 for transitioning tensioning mechanism 330 between the generally un-tensioned state (FIG. 3B) and the tensioned state (FIG. 3C). That is, with third roller 346 disposed in the raised position, third roller 346 is in closer proximity to both first and second rollers 342, 344, respectively, and, thus, belt 340 is relatively less tensioned. This corresponds to the generally un-tensioned state of tensioning mechanism 330 shown in FIG. 3B. On the other hand, when third roller 346 is disposed in the lowered position, third roller 346 is further spaced from both first and second rollers 342, 344, respectively, such that belt 340 is tensioned. This corresponds to the tensioned state of tensioning mechanism 330 shown in FIG. 3C.

Each motor 362, 364 is coupled to one of the ends of third support bar 347 such that, upon actuation of motors 362, 364, third support bar 347 and, thus, third roller 346 are raised or lowered to transition tensioning mechanism 330 between the generally un-tensioned state and the tensioned state. A cable (or cables) 366 couples motors 362, 364 to the energy source, e.g., generator 40 (FIG. 1A) or internal energy source 50 (FIG. 1C), for providing power to motors 362, 364. Motors 362, 364 may be actuated manually, e.g., via squeezing movable handle 24, activating one or more of switch assemblies 30, 32 or trigger assembly 25 (see FIG. 1A), or via any other suitable mechanism. Alternatively, motors 362, 364 may be automatically actuated, e.g., via one or more sensors (not explicitly shown) configured to sense the properties of jaw members 310, 320 and/or tissue. However, although motors 362, 364 may be actuated manually, motors 362, 364 are configured to automatically translate third support bar 347 according to a pre-determined function, e.g., at a pre-determined rate (variable or constant rate), at pre-determined intervals, upon sensing a particular condition, etc., thus eliminating the inaccuracies associated with manually-controlled movement of third support bar 347. As an alternative to motors 362, 364, third support bar 347 may be driven by any other suitable mechanism such as those discussed above with respect to end effector assembly 200 (FIGS. 2A-2C).

With continued reference to FIGS. 3A-3C, the operation of end effector assembly 300 is described. Initially, jaw members 310, 320 are disposed in the spaced-apart position and tensioning mechanism 330 is disposed in the generally un-tensioned state, e.g., third roller 346 is disposed in closer proximity to first and second rollers 342, 344. In this position, end effector assembly 300 may be manipulated and/or maneuvered into position such that tissue to be treated, e.g., sealed and/or cut, is disposed between jaw members 310, 320.

Next, with reference to FIG. 3B, movable handle 24 (FIG. 1A) is squeezed towards fixed handle 26 (FIG. 1A), or jaw members 310, 320 are otherwise moved relative to one another, such that jaw members 310, 320 are pivoted relative to one another from the spaced-apart position to the approximated position to grasp tissue therebetween. As jaw members 310, 320 are approximated relative to one another, pressure is applied to tissue therebetween. However, at this point, the pressure applied to tissue grasped between jaw members 310, 320 is relatively small since tensioning mechanism 330 is disposed in the generally un-tensioned state. That is, with tensioning mechanism 330 disposed in the generally un-tensioned state, tissue grasped between jaw members 310, 320 urges the portion of belt 340 forming tissue contacting surface 322 inwardly due to the reduced tension on belt 340. As such, this inward movement, or bowing, of belt 340 reduces the pressure exerted on tissue disposed between tissue contacting member 314 of jaw member 310 and tissue contacting surface 322 of belt 340 of jaw member 320.

Continuing with reference to FIG. 3B, with jaw members 310, 320 disposed in the approximated position and grasping tissue between tissue contacting member 314 and tissue contacting surface 322 of jaw members 310, 320, respectively, and with tensioning mechanism 330 disposed in the generally un-tensioned state, energy may be transmitted from energy transmission member 350 of jaw member 320, through tissue, to tissue contacting member 314 of jaw member 310, as indicated by arrows "A" (although energy may alternatively be transmitted in the opposite direction, or in both directions). Activation of the light energy may be effected via actuating one or more of first and second switch assemblies 30 and 32 (FIG. 1A), or via any other suitable mechanism.

As mentioned above, with jaw members 310, 320 initially applying a relatively smaller pressure to tissue (as a result of tensioning mechanism 330 being disposed in the generally un-tensioned state), maximum absorption of light energy by tissue at the beginning of the sealing cycle is effected. Once tissue has absorbed a sufficient amount of energy, upon satisfaction of a pre-determined condition, time, and/or function, or upon manual or other suitable automatic actuation, motors 362, 364 (or any other suitable mechanism configured to translate third roller 346) may be activated. Upon activation of motors 362, 364 third support bar 347 and, thus, third roller 346 is move further into cavity 326 of jaw member 320 and away from first and second rollers 342, 344, respectively, to transition tensioning mechanism 330 to the more tensioned state. Motors 362, 364 may be configured to move third support bar 347 a constant or variable rate and/or either continuously or incrementally, or according to any other suitable pre-determined function (or functions), similarly as described above with respect to motor 250 of end effector assembly 200 (FIGS. 2A-2C).

Referring to FIG. 3C, as motors 362, 364 translate third roller 346 towards first and second rollers 342, 344, respectively, i.e., as tensioning mechanism 330 is transitioned form the generally un-tensioned state towards the tensioned state, belt 340 is tensioned, or pulled more taught such that the inward bowing, or flexion of the portion of belt 340 forming tissue contacting surface 322 is eliminated, i.e., such that the portion of belt 340 forming tissue contacting surface 322 and the opposed surface of jaw member 320 define a more planar configuration. As a result of this, belt 340 exerts an increased pressure on tissue, urging tissue towards tissue contacting member 314 of jaw member 310, thus increasing the pressure exerted on tissue disposed between tissue contacting member 314 of jaw member 310 and tissue contacting surface 322 of belt 340 of jaw member 320.

With tensioning mechanism 330 disposed in the tensioned state such that jaw members 310, 320 grasp tissue under an increased pressure, the transmission of energy from energy transmission member 350 of jaw member 320, through tissue, to tissue contacting member 314 of jaw member 310 may be continued to complete formation of a tissue seal and/or to divide tissue along the previously formed tissue seal. Alternatively, tensioning mechanism 330 may be transitioned to an intermediate state for completion of the tissue seal, and may then be moved to the tensioned state for cutting tissue along the previously formed tissue seal. At the completion of tissue treatment, e.g., sealing and/or cutting of tissue, jaw members 310, 320 are returned to the spaced-apart position and end effector assembly 300 is removed from the surgical site (or is repositioned adjacent other tissue to be treated).

Referring to FIGS. 4A-4D, another embodiment of an end effector assembly 400 is shown defining a longitudinal axis "X-X" and generally including first and second jaw members 410, 420, respectively, that are movable relative to one another between a spaced-apart position and an approximated position (FIGS. 4A-4D) for grasping tissue therebetween.

One of the jaw members, e.g., jaw member 410, includes a tissue contacting member 414 disposed on or along surface 412 thereof that is configured to facilitate the transmission of light energy from the light energy source, e.g., generator 40 (FIG. 1A) or internal energy source 50 (FIG. 1C), to tissue grasped between jaw members 410, 420. That is, tissue contacting member 414 of jaw member 410 may be coupled to the light energy source, e.g., via cable 416, such that light energy may be transmitted from jaw member 410, through tissue grasped between jaw members 410, 420, and to jaw member 420, as indicated by arrows "A." Alternatively, tissue contacting member 414 may be configured to receive light energy, e.g., absorb or reflect light energy, in embodiments where light energy is transmitted from jaw member 420 towards jaw member 410.

The other jaw member (or both jaw members), e.g., jaw member 420, includes an inflatable member 430 disposed within a cavity 426 defined within jaw member 420. Inflatable member 430 is formed at least partially from a resilient, fluid-tight material and includes an internal chamber (not explicitly shown) adapted to receive (or expel) inflation fluids, e.g., gas and/or liquid, to inflate (or deflate) inflatable member 430. Inflatable member 430 further includes an exposed surface defining at least a portion of tissue contacting surface 422 of jaw member 420. Tissue contacting surface 422 of inflatable member 430 is disposed in opposing relation relative to tissue contacting member 414 of jaw member 410 such that, upon approximation of jaw members 410, 420, tissue is grasped between tissue contacting member 414 of jaw member 410 and tissue contacting surface 422 of inflatable member 430 of jaw member 420.

As best shown in FIGS. 4A and 4C, Inflatable member 430 may be coupled to a fluid source (not explicitly shown) via valve 432 and conduit 434 for selectively inflating and/or deflating inflatable member 430. Alternatively, inflatable member 430 may be self-contained. As will be described in greater detail below, inflatable member 430 is selectively transitionable between a generally deflated state (FIGS. 4A and 4B) and an inflated state (FIGS. 4C and 4D) for selectively varying the pressure applied to tissue grasped between jaw members 410, 420.

In embodiments where inflatable member 430 is coupled to a fluid source (not explicitly shown) via valve 432 and conduit 434, the supply of fluid to/from inflatable member 430 to inflate/deflate inflatable member 430 may be actuated manually, e.g., via squeezing movable handle 24, activating one or more of switch assemblies 30, 32 or trigger assembly 25 (see FIG. 1A), or via any other suitable mechanism. Alternatively, the supply of fluid may be automatically actuated, e.g., via one or more sensors (not explicitly shown) configured to sense the properties of jaw members 410, 420 and/or tissue.

In embodiments where inflatable member 430 is self-contained, the internal chamber of inflatable member 430 may be sealed and filled with a pre-determined volume of liquid such that, upon heating of inflatable member 430 to a pre-determined temperature (the boiling point of the liquid), the liquid is transformed at least partially into a gas, thereby expanding inflatable member 430. Heating of inflatable member 430 may be effected via the absorption of light energy from tissue contacting member 414 of jaw member 410, through tissue, and to jaw member 420, via the heat generated during tissue treatment, via one or more heaters (not shown), disposed within jaw member 420, or via any other suitable mechanism. In these embodiments, inflation of inflatable member 430 may be effected automatically, e.g., once inflatable member 430 has absorbed a sufficient amount of light energy to sufficiently heat the fluid disposed therein, or via manual actuation, e.g., via activating the heaters (not shown).

Inflatable member 430, as best shown in FIGS. 4A and 4C, may further include one or more relief valves 436 operably disposed thereon. Relief valves 436 are configured to regulate the pressure within inflatable member 430 by releasing a sufficient amount of fluid from inflatable member 430 when necessary to maintain the pressure within inflatable member 430 below a pre-determined threshold. Such a feature not only inhibits over-inflation (and potentially bursting) of inflatable member 430, but may also be used to intentionally apply fluids to jaw members 410, 420 and/or tissue during tissue treatment. Such fluids may be used to treat tissue, help cool the surrounding area, inhibit sticking of tissue to jaw members 410, 420, and/or to clean tissue contacting member 414 or other portions of end effector assembly 400. As an alternative to relief valve(s) 436, inflatable member 430 may include perforations (not explicitly shown), micro-apertures (not explicitly shown), or other suitable features configured to leak either continuously or upon reaching a pre-determined pressure, thereby helping to inhibit over-inflation of inflatable member 430 and/or to supply fluids to jaw members 410, 420, tissue, and the surrounding area.

With continued reference to FIGS. 4A-4D, the operation of end effector assembly 400 is described. Initially, jaw members 410, 420 are disposed in the spaced-apart position and inflatable member 430 is disposed in the generally deflated state (FIGS. 4A and 4B). In this position, end effector assembly 400 may be manipulated and/or maneuvered into position such that tissue to be treated, e.g., sealed and/or cut, is disposed between jaw members 410, 420.

Next, referring to FIGS. 4A and 4B, movable handle 24 (FIG. 1A) is squeezed towards fixed handle 26 (FIG. 1A), or jaw members 410, 420 are otherwise moved relative to one another, such that jaw members 410, 420 are pivoted relative to one another from the spaced-apart position to the approximated position to grasp tissue therebetween. As jaw members 410, 420 are approximated relative to one another, pressure is applied to tissue therebetween. However, at this point, the pressure applied to tissue grasped between jaw members 410, 420 is relatively small since inflatable member 430 is disposed in the generally deflated state. More specifically, with inflatable member 430 disposed in the generally deflated state, tissue grasped between jaw members 410, 420 is permitted to enter at least a portion of cavity 426 defined within jaw member 420 since inflatable member 430 is generally deflated and, thus, does not fully occupy cavity 426. As a result, the pressure exerted on tissue disposed between jaw members 410, 420 is relatively smaller.

With jaw members 410, 420 disposed in the approximated position and grasping tissue between tissue contacting member 414 and tissue contacting surface 422 of jaw members 410, 420, respectively, and with inflatable member 430 disposed in the generally deflated state, energy may be transmitted from tissue contacting member 414 of jaw member 410, through tissue, to tissue contacting surface 422 of jaw member 420, as indicated by arrows "A" (although energy may alternatively be transmitted in the opposite direction, or in both directions). Activation of the light energy may be effected via actuating one or more of first and second switch assemblies 30 and 32 (FIG. 1A), or via any other suitable mechanism. Since inflatable member 430 is disposed in the generally deflated state at this point, jaw members 410, 420 are applying a relatively smaller pressure to tissue, thereby maximizing the absorption of light energy by tissue.

Once tissue has absorbed a sufficient amount of energy, upon satisfaction of a pre-determined condition, time, and/or function, or upon manual or other suitable automatic actuation, inflatable member 430 may be inflated, e.g., via actuation of trigger assembly 25 (FIG. 1A), one or more of switch assemblies 30, 32 (FIG. 1A), or via any other suitable mechanism. The inflow of fluid into inflatable member 430 (or the transitioning of the liquid disposed therein to gas), causes inflatable member 430 to inflate or expand towards the inflated state. Inflatable member 430 may be inflated at a constant or variable rate, either continuously or in increments, or according to any other suitable pre-determined function (or functions).

Turning to FIGS. 4C-4D, as inflatable member 430 is increasingly inflated, inflatable member 430 increasingly fills, or occupies cavity 426 defined within jaw member 420, thereby urging tissue from cavity 426 towards jaw member 410. This urging of tissue towards jaw member 410 increases the pressure exerted on tissue disposed between tissue contacting member 414 of jaw member 410 and tissue contacting surface 422 of inflatable member 430 of jaw member 420. With jaw members 410, 420 disposed in the approximated position and grasping tissue between tissue contacting member 414 and tissue contacting surface 422 of jaw members 410, 420, respectively, and with inflatable member 430 disposed in the inflated state, energy may be continued to be transmitted from tissue contacting member 414 of jaw member 410, through tissue, to tissue contacting surface 422 of jaw member 420, as indicated by arrows "A" (although energy may alternatively be transmitted in the opposite direction, or in both directions). Activation of the light energy may be effected via actuating one or more of first and second switch assemblies 30 and 32 (FIG. 1A), or via any other suitable mechanism. As described above with respect to end effector assemblies 200 and 300 (FIGS. 2A-2C and 3A-3C, respectively), initially applying a relatively smaller pressure to tissue maximizes absorption of light energy by tissue, while subsequently applying an increased pressure facilitates the complete formation of a tissue seal and/or the division of tissue along the previously formed tissue seal.

Continuing with reference to FIGS. 4C-4D, inflatable member 430, as mentioned above, may further be configured to include one or more relief valves 436 (or other features) to inhibit over-inflation and/or supply fluids to jaw members 410, 420, tissue, and/or the surrounding area. As such, upon inflation of inflatable member 430 to a pre-determined pressure (e.g., the inflated state) to complete the tissue seal and/or divide tissue, fluids may be supplied to jaw members 410, 420 and/or tissue to further treat tissue, cool tissue, clean jaw members 410, 420, or for any other suitable purpose. Thus, end effector assembly 400 may be utilized to initially apply a smaller pressure to maximize light energy absorption, to apply an increased pressure to complete formation of a tissue seal and/or to cut tissue, and/or to supply fluid to jaw members 410, 420 and/or tissue to facilitate formation of the tissue seal, cutting of tissue, cleaning of one or more components of end effector assembly 400, or for other purposes.

Once tissue treatment, e.g., sealing and/or cutting of tissue, is complete, jaw members 410, 420 are returned to the spaced-apart position and end effector assembly 400 is repositioned adjacent other tissue to be treated (or is removed from the surgical site). As mentioned above, the supply of fluid from inflatable member 430 to jaw members 410, 420 may be used to clean tissue contacting member 414 of jaw member 410 so as not to obscure the transmission of light energy therefrom during subsequent tissue treatment.

Referring to FIGS. 5A-5F, another embodiment of an end effector assembly 500 is shown disposed at distal end 16 of shaft 12. End effector assembly 500 defines a longitudinal axis "X-X" and generally includes first and second jaw members 510, 520, respectively, that are movable relative to one another between a spaced-apart position, a first approximated position, and a second approximated position for grasping tissue therebetween. Jaw members 510, 520 are biased towards the spaced-apart position by a biasing member, e.g., via a torsion spring (not shown) disposed about the pivot pin (not shown), or via any other suitable biasing member (not shown).

One or both of the jaw members, e.g., jaw member 510, includes a tissue contacting member 514 disposed on or along surface 512 that is configured to facilitate the transmission of light energy from the light energy source, e.g., generator 40 (FIG. 1A) or internal energy source 50 (FIG. 1C), to tissue grasped between jaw members 510, 520, similarly as described above with respect to any of end effector assemblies 200, 300, 400 (FIGS. 2A-2C, 3A-3C, 4A-4D, respectively). The other jaw member, e.g., jaw member 520, includes a tissue contacting surface 522 (or tissue contacting member similar to tissue contacting member 514) that is configured to receive, absorb, or reflect the light energy transmitted from jaw member 510 and through tissue.

End effector assembly 500 further includes a closure mechanism 530 engaged at the distal end of a drive bar 532 that is disposed within shaft 12. Drive bar 532 is longitudinally translatable through and relative to shaft 12 and is ultimately coupled to the drive assembly (not shown) and movable handle 24 of forceps 10 (FIG. 1A) such that jaw members 510, 520 of end effector assembly 500 are movable between the spaced-apart, first approximated, and second approximated positions upon manipulation of movable handle 24, as will be described in greater detail below.

Figure 5A:
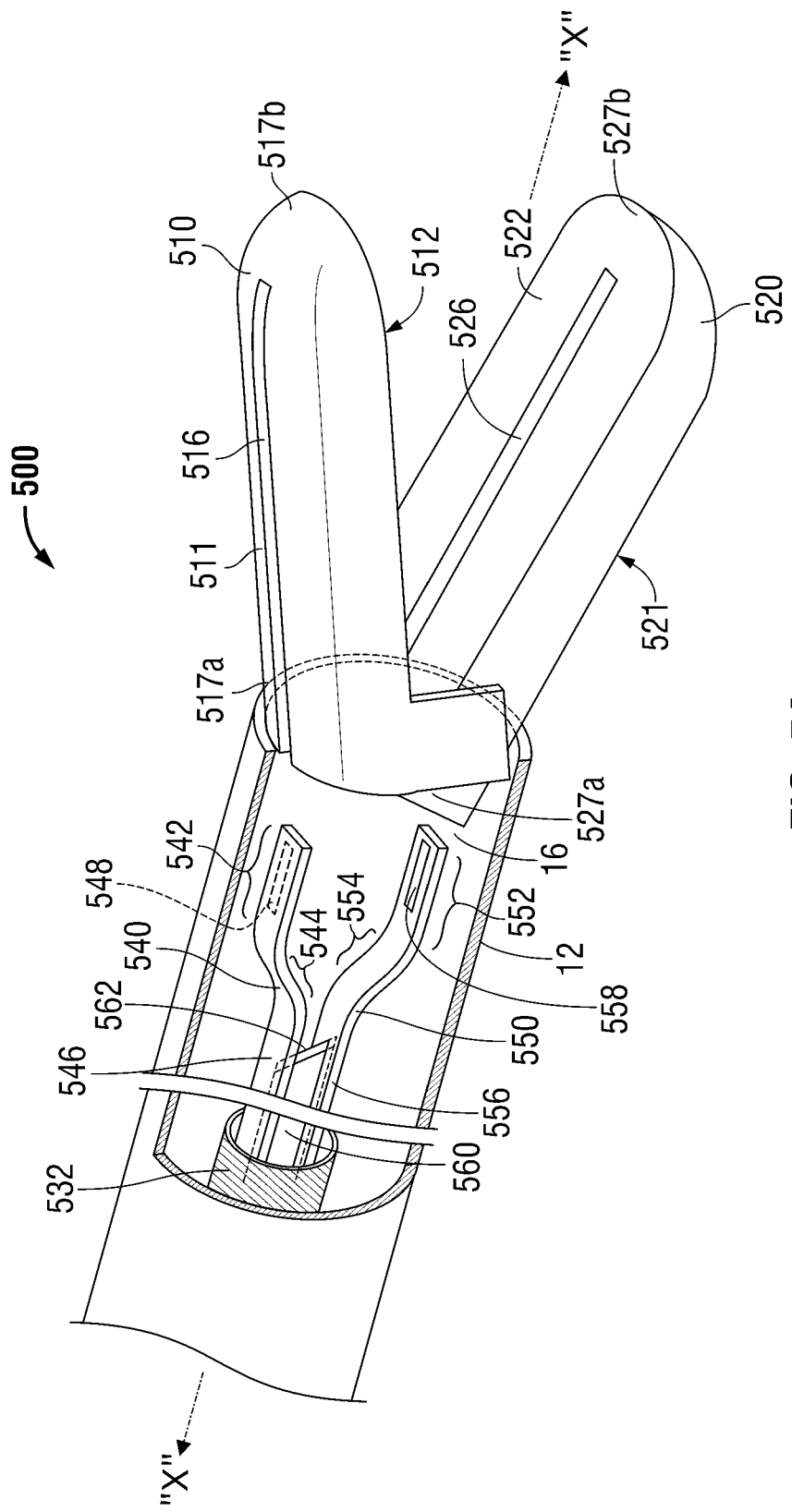
FIG. 5A is an enlarged, side, cut-away view of another embodiment of an end effector assembly provided in accordance with the present disclosure, wherein jaw members of the end effector assembly are disposed in a spaced-apart position.

Continuing with reference to FIGS. 5A-5F and to FIG. 5A in particular, each jaw member 510, 520 includes an outer surface 511, 521, respectively, and an opposed surface 512, 522, respectively. Jaw members 510, 520 each further include a longitudinally-extending slot 516, 526, respectively, extending from the respective proximal end 517a, 527a towards the respective distal end 517b, 527b thereof. Due to this configuration, jaw members 510, 520 define open proximal ends 517a, 527a, respectively, that provide access to slots 516, 526, while distal ends 517b, 527b, of jaw members 510, 520, respectively, defined closed ends of respective slots 516, 526. As will be detailed below, slots 516, 526 defined within jaw members 510, 520, respectively, are configured to permit translation of closure mechanism 530 therethrough to transition jaw members 510, 520 between the spaced-apart, first approximated, and second approximated positions.

Figure 5B:
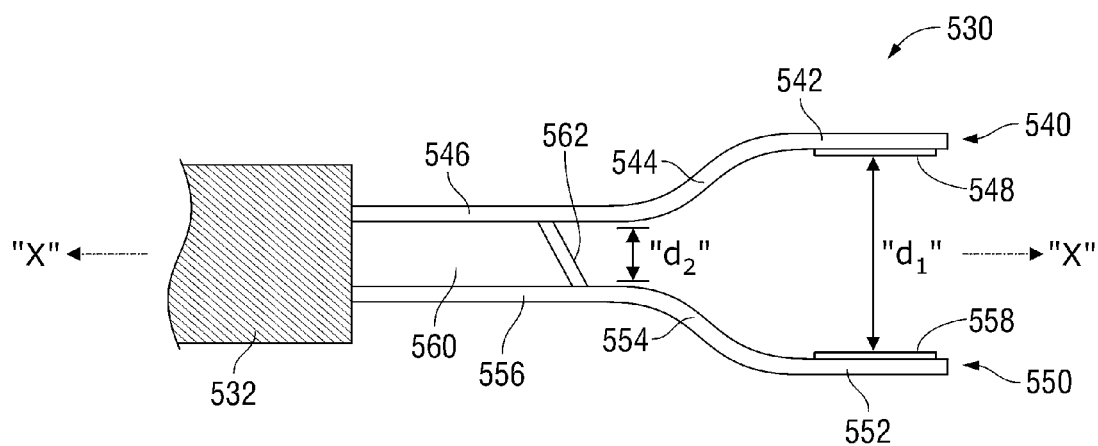
FIG. 5B is an enlarged, side view of a closure mechanism of the end effector assembly of FIG. 5A.

Closure mechanism 530, as best shown in FIGS. 5A-5B, and as mentioned above, is engaged at the distal end of drive bar 532. Closure mechanism 530 includes first and second spaced-apart transverse beams 540, 550, respectively, and a perpendicular beam 560 interconnecting first and second transverse beams 540, 550, respectively. First and second transverse beams 540, 550 each include a distal portion 542, 552, an intermediate portion 544, 554 and a proximal portion 546, 556, respectively. Distal portions 542, 552 of first and second transverse beams 540, 550, respectively, define a first distance "$d_1$" therebetween, while proximal portions 546, 556, of first and second transverse beams 540, 550, respectively, define a second, smaller distance "$d_2$" therebetween. Intermediate portions 544, 554 of first and second transverse beams 540, 550, respectively, define sloped configurations so as to interconnect the distal and proximal portions 542, 552 and 546, 556, respectively, of first and second transverse beams 540, 550. Further, distal portions 542, 552 and/or intermediate portions 544, 554 of first and second transverse beams 540, 550, respectively, may each include a perpendicular spine 548, 558 extending therefrom to facilitate proper closure of jaw members 510, 520, as will be described in greater detail below.

Perpendicular beam 560 is engaged to and extends between first and second transverse beams 540, 550 along at least a portion of the proximal portions 546, 556, respectively, thereof to retain first and second transverse beams 540, 550 in fixed position relative to one another. In some embodiments, perpendicular beam 560 defines a distal cutting blade 562 for cutting tissue grasped between jaw members 510, 520, as will be described below.

Figure 5C:
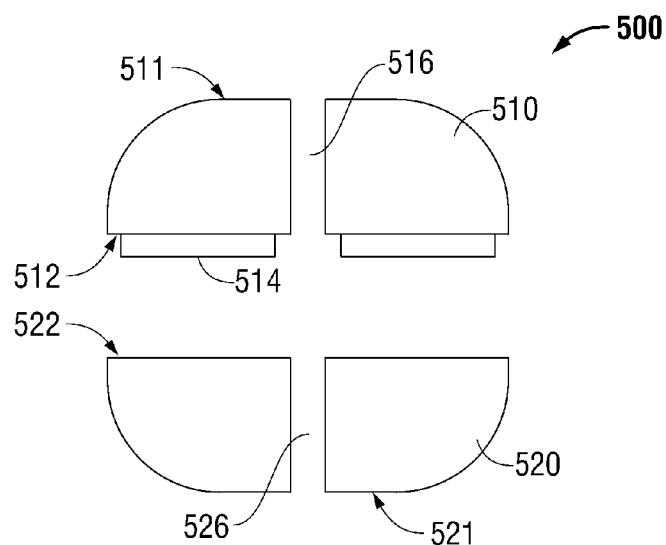
FIG. 5C is an enlarged, transverse cross-sectional view of the end effector assembly of FIG. 5A, wherein the jaw members are disposed in a spaced-apart position.

Referring to FIGS. 5C-5F, in conjunction with FIGS. 5A-5B, the operation of end effector assembly 500 is described. Initially, as shown in FIGS. 5A and 5C, jaw members 510, 520 are disposed in the spaced-apart position. More specifically, with closure mechanism 530 disposed within shaft 12 and positioned proximally of jaw members 510, 520, jaw members 510, 520 are maintained under bias in the spaced-apart position. In this position, end effector assembly 500 may be manipulated and/or maneuvered into position such that tissue to be treated, e.g., sealed and/or cut, is disposed between jaw members 510, 520.

Figure 5D:
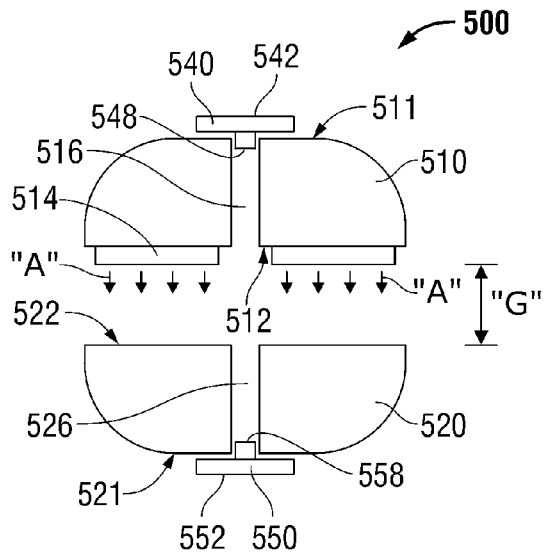
FIG. 5D is an enlarged, transverse cross-sectional view of the end effector assembly of FIG. 5A, wherein the jaw members are disposed in a first approximated position.

Turning to FIG. 5D, in conjunction with FIGS. 5A-5B, with tissue to be treated in position between jaw members 510, 520, movable handle 24 (FIG. 1A) is pulled proximally relative to fixed handle 26 (FIG. 1A), or the drive assembly (not shown) is otherwise activated such that drive bar 532 is translated distally though shaft 12 to similarly translate closure mechanism 530 distally relative to shaft 12 and jaw members 510, 520. As closure mechanism 530 is advanced further distally towards jaw members 510 520, first and second transverse beams 540, 550 eventually contact outer surfaces 511, 521 of jaw members 510, 520, respectively, while spines 548, 558 (in embodiments where spines 548, 558 are provided) enter slots 516, 526, respectively, from proximal ends 517a, 527a of jaw members 510, 520. Transverse beams 540, 550 are advanced distally about outer surfaces 511, 521 of jaw members 510, 520 until distal portions 542, 552 of transverse beams 540, 550, are substantially disposed about jaw members 510, 520, thereby urging jaw members 510, 520 towards one another from the spaced-apart position to the first approximated position to grasp tissue therebetween, as shown in FIG. 5C. At the same time, spines 548, 558 enter slots 516, 526 to help ensure proper closure of jaw members 510, 520 and to help inhibit splaying of jaw members 510, 520 when closing about tissue. However, it is noted that spines 548, 558 do not extend beyond surfaces 512, 522 of jaw members 510, 520, respectively, so as not to interfere with the grasping of tissue therebetween. Referring also to FIG. 1A, jaw members 510, 520 may be retained in this first approximated position via latching of latch assembly 27 which, as mentioned above, locks movable handle 24 at one or more positions between the initial position and the compressed position.

In this first approximated position, wherein distal portions 542, 552 of transverse beams 540, 550, respectively, are disposed about jaw members 510, 520, tissue contacting member 514 and tissue contacting surface 522 of jaw members 510, 520, respectively, define a first gap distance "G" therebetween. First gap distance "G" is defined by the first distance "$d_1$" between transverse beams 540, 550 and the thickness of jaw members 510, 520. Thus, as can be appreciated, a desired first gap distance "G" between tissue contacting member 514 and tissue contacting surface 522 of jaw members 510, 520, respectively, may be achieve by configuring closure mechanism 530 to define a corresponding distance "$d_1$" between first and second transverse beams 540, 550 thereof, taking into account the thickness of jaw members 510, 520.

Continuing with reference to FIG. 5D, with jaw members 510, 520 disposed in the first approximated position grasping tissue therebetween, light energy may be transmitted from tissue contacting member 514 of jaw member 510, through tissue, to tissue contacting surface 522 of jaw member 520, as indicated by arrows "A" (although energy may alternatively be transmitted in the opposite direction or in both directions). Activation of the energy may be effected via actuating one or more of first and second switch assemblies 30 and 32 (FIG. 1A). As mentioned above, with distal portions 542, 552 of transverse beams 540, 550 disposed about jaw members 510, 520, respectively, jaw members 510, 520 are disposed in the first approximated position, as shown in FIG. 5C wherein a gap distance "G" is defined between surfaces 512, 522 of jaw members 510, 520, respectively. As a result of this relatively larger gap distance "G" between jaw members 510, 520, a relatively smaller pressure is applied to tissue grasped between jaw members 510, 520 and, thus, the absorption of light energy by tissue grasped between jaw members 510, 520 is maximized.

Figure 5E:
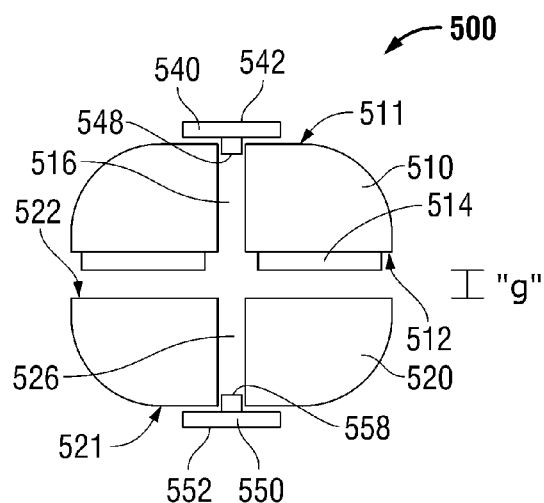
FIG. 5E is an enlarged, transverse cross-sectional view of the end effector assembly of FIG. 5A, wherein the jaw members are disposed in a second approximated position.

Referring to FIG. 5E, once tissue has absorbed a sufficient amount of energy, upon satisfaction of a pre-determined condition, time, and/or function, or upon manual or other suitable automatic actuation, movable handle 24 (FIG. 1A) is squeezed further towards fixed handle 26 (FIG. 1A) such that drive bar 532 and closure mechanism 530 are translated further distally through shaft 12 and relative to jaw members 510, 520. As closure mechanism 530 is advanced further distally relative to jaw members 510, 520, intermediate portions 544, 554 of transverse beams 540, 550, respectively, are urged into contact with, and are translated distally along outer surfaces 511, 521 of jaw members 510, 520, respectively. The inward sloping of intermediate portions 544, 554 of transverse beams 540, 550, respectively, towards one another urged jaw members 510, 520 further towards one another. Upon further distal translation of closure mechanism 530, proximal portions 546, 556 of transverse beams 540, 550, respectively, are disposed substantially about jaw members 510, 520.

With proximal portions 546, 556 of transverse beams 540, 550, respectively, disposed about jaw members 510, 520, respectively, jaw members 510, 520 are disposed in the second approximated position. In the second approximated position, tissue contacting member 514 and tissue contacting surface 522 of jaw members 510, 520, respectively, are urged further towards one another to define a second, smaller gap distance "g" therebetween as a result of the reduced distance "$d_2$" between proximal portions 546, 556 of transverse beams 540, 550, respectively, as compared to the distance "$d_1$" between distal portions 542, 552 of transverse beams 540, 550, respectively. As a result of proximal portions 546, 556 of transverse beams 540, 550, respectively, urging jaw members 510, 520 further towards one another to define this relatively smaller gap distance "g" therebetween, a relatively greater pressure is applied to tissue grasped between jaw members 510, 520 in the second approximated position as compared to the first approximated position. In this second approximated position, wherein a greater pressure is applied to tissue, the transmission of energy from tissue contacting member 514 of jaw member 510, through tissue, to tissue contacting surface 522 of jaw member 520 may be continued to complete formation of the tissue seal. Similarly as described above with respect to the first approximated position, latching assembly 27 (FIG. 1A) may also be utilized to lock jaw members 510, 520 in this second approximated position.

Figure 5F:
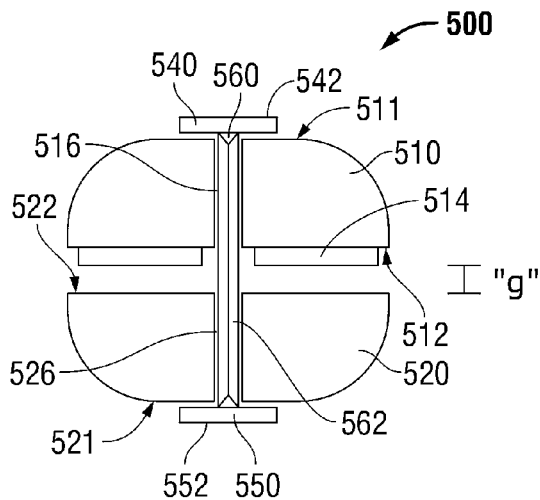
FIG. 5F is an enlarged, transverse cross-sectional view of the end effector assembly of FIG. 5A, wherein a knife blade of the closure mechanism is advanced between the jaw members.

Turning now to FIG. 5F, upon completion of the tissue seal (or where only tissue division is desired), closure mechanism 530 may be advanced further distally, e.g., via further squeezing of movable handle 24 towards fixed handle 26 (FIG. 1A), such that perpendicular beam 560, lead by distal knife blade 562, is advanced through slots 516, 526 defined within jaw members 510, 520, respectively. As can be appreciated, distal knife blade 562 may be positioned further proximally or distally relative to transverse beams 540, 550 such that cutting of tissue is effected near simultaneously after complete formation of the tissue seal, or such that movement of jaw members 510, 520 to the second approximated position and cutting of tissue grasped between jaw members 510, 520 are discrete steps. Further, closure mechanism 530 may include various different portions defining various different distances therebetween such that end effector assembly 500 may include a third, fourth, etc. approximated position to facilitate treating various tissue sizes and types and/or for use in various different tissue treatment procedures.

At the completion of tissue treatment, e.g., sealing and/or cutting of tissue, movable handle 24 (FIG. 1A) may be released, or drive bar 532 may be otherwise translated proximally such that closure mechanism 530 is likewise translated proximally back into shaft 12, thus permitting jaw members 510, 520 to return under bias to the spaced-apart position. Thereafter, end effector assembly 500 may be removed from the surgical site (or may be repositioned adjacent other tissue to be treated).

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A forceps, comprising:
an end effector assembly including first and second jaw members coupled to one another and movable between a spaced-apart position, a first approximated position, and a second approximated position, each of the first and second jaw members including an opposed tissue-contacting surface, at least one of the first and second jaw members adapted to connect to a source of energy for transmitting energy to tissue disposed between the opposed tissue-contacting surfaces; and
a closure mechanism operably associated with the end effector assembly, the closure mechanism including a distal portion, an intermediate portion, and a proximal portion, the closure mechanism movable relative to the end effector assembly between a first position, wherein the closure mechanism is positioned proximally of the end effector assembly and the first and second jaw members are disposed in the spaced-apart position, a second position, wherein the distal portion of the closure mechanism is operably engaged with the end effector assembly and the first and second jaw members are disposed in the first approximated position, a third position, wherein the intermediate portion of the closure mechanism is operably engaged with the end effector assembly and the first and second jaw members are disposed between the first and second approximated positions, and a fourth position, wherein the proximal portion of the closure mechanism is operably engaged with the end effector assembly and the first and second jaw members are disposed in the second approximated position, the distal, intermediate, and proximal portions of the closure mechanism defining different configurations.

2. The forceps according to claim 1, wherein, in the first approximated position, a first gap distance is defined between the tissue-contacting surfaces of the first and second jaw members and wherein, in the second approximated position, a second, smaller gap distance is defined between the tissue-contacting surfaces of the first and second jaw members.

3. The forceps according to claim 1, wherein, in the first approximated position, the first and second jaw members are configured to apply a first grasping pressure to tissue disposed between the tissue-contacting surfaces and wherein, in the second approximated position, the first and second jaw members are configured to apply a second, greater grasping pressure to tissue disposed between the tissue-contacting surfaces.

4. The forceps according to claim 1, wherein at least one of the first and second jaw members is adapted to connect to a source of light energy for treating tissue disposed between the tissue-contacting surfaces.

5. The forceps according to claim 1, wherein the closure mechanism includes first and second spaced-apart beams, the first beam configured to engaged the first jaw member and the second beam configured to engage the second jaw member.

6. The forceps according to claim 5, wherein the first and second beams are spaced-apart a first distance relative to one another in the distal portion of the closure mechanism and wherein the first and second beams are spaced-apart a second, smaller distance relative to one another in the proximal portion of the closure mechanism.

7. The forceps according to claim 6, wherein the first and second beams are parallel to one another in the distal and proximal portions of the closure mechanism, and wherein the first and second beams are non-parallel relative to one another in the intermediate portion of the closure mechanism.

8. The forceps according to claim 5, further including a knife disposed between the first and second spaced-apart beams.

9. The forceps according to claim 8, wherein the knife is positioned in the proximal portion of the closure mechanism such that, in the fourth position of the closure mechanism, the knife is disposed between the first and second jaw members for cutting tissue therebetween.

10. The forceps according to claim 1, further including a housing having a shaft that extends therefrom, wherein the closure mechanism is slidably disposed within the shaft.

11. The forceps according to claim 10, further including a drive bar slidably disposed within the shaft and coupled to the closure mechanism, the drive bar translatable through the shaft for translating the closure mechanism relative to the end effector assembly.

12. The forceps according to claim 11, further including:
a handle assembly associated with the housing and operably coupled to the drive bar, the handle assembly including a movable handle movable between an initial position, a first compressed position, an intermediate compressed position, and a second compressed position for moving the closure mechanism between the respective first, second, third, and fourth positions.

13. A forceps, comprising:
a housing;
a shaft extending distally from the housing;
an end effector assembly disposed at a distal end of the shaft, the end effector assembly including first and second jaw members pivotably coupled to one another, at least one of the first and second jaw members movable relative to the other between a spaced-apart position, a first approximated position, and a second approximated position, each of the first and second jaw members defining an opposed tissue-contacting surface, at least one of the first and second jaw members adapted to connect to a source of energy for transmitting energy to tissue disposed between the opposed tissue-contacting surfaces; and
a closure mechanism slidably disposed within the shaft, the closure mechanism including a pair of beams each defining a distal portion and a proximal portion, the distal portions of the beams defining a first distance therebetween and the proximal portions of the beams defining a second, smaller distance therebetween, the closure mechanism translatable through the shaft and relative to the end effector assembly between a first position, wherein the beams are positioned within the shaft proximally of the end effector assembly and the first and second jaw members are disposed in the spaced-apart position, a second position, wherein the distal portions of the beams are positioned to surround the first and second jaw members and urge the first and second jaw members to the first approximated position, and a third position, wherein the proximal portions of the beams are positioned to surround the first and second jaw members and urge the first and second jaw members to the second approximated position.

14. The forceps according to claim 13, wherein, in the first approximated position, a first gap distance is defined between the tissue-contacting surfaces of the first and second jaw members and wherein, in the second approximated position, a second, smaller gap distance is defined between the tissue-contacting surfaces of the first and second jaw members.

15. The forceps according to claim 13, wherein, in the first approximated position, the first and second jaw members are configured to apply a first grasping pressure to tissue disposed between the tissue-contacting surfaces and wherein, in the second approximated position, the first and second jaw members are configured to apply a second, greater grasping pressure to tissue disposed between the tissue-contacting surfaces.

16. The forceps according to claim 13, wherein at least one of the first and second jaw members is adapted to connect to a source of light energy for treating tissue disposed between the tissue-contacting surfaces.

17. The forceps according to claim 13, wherein the closure mechanism further includes a third beam interconnecting the first and second beams.

18. The forceps according to claim 17, wherein the first and second jaw members each defines a slot extending therethrough, the third beam configured to translate through the slots of the first and second jaw members upon movement of the closure mechanism between the second and third positions.

19. The forceps according to claim 13, further including a handle assembly associated with the housing and operably coupled to the closure mechanism, the handle assembly including a movable handle movable between an initial position, a first compressed position, and a second compressed position for moving the closure mechanism between the respective first, second, and third positions.

* * * * *